US009526876B2

(12) United States Patent
Kristensen et al.

(10) Patent No.: US 9,526,876 B2
(45) Date of Patent: Dec. 27, 2016

(54) CATHETER GUIDING DEVICE

(75) Inventors: Peter Heydorn Kristensen, Knebel (DK); Niels Katballe, Lystrup (DK)

(73) Assignee: Pieuratech APS, Arhus N (DK)

(*) Notice: Subject to any disclaimer, the term of this patent is extended or adjusted under 35 U.S.C. 154(b) by 296 days.

(21) Appl. No.: 13/697,256

(22) PCT Filed: May 10, 2011

(86) PCT No.: PCT/EP2011/002325
§ 371 (c)(1),
(2), (4) Date: Dec. 17, 2012

(87) PCT Pub. No.: WO2011/141162
PCT Pub. Date: Nov. 17, 2011

(65) Prior Publication Data
US 2013/0131549 A1 May 23, 2013

Related U.S. Application Data

(60) Provisional application No. 61/333,415, filed on May 11, 2010.

(30) Foreign Application Priority Data

May 11, 2010 (DK) ................................ 2010 70200

(51) Int. Cl.
*A61D 5/00* (2006.01)
*A61M 27/00* (2006.01)
(Continued)

(52) U.S. Cl.
CPC .......... *A61M 27/00* (2013.01); *A61B 10/0045* (2013.01); *A61B 17/3415* (2013.01);
(Continued)

(58) Field of Classification Search
CPC .... A61M 25/00; A61B 10/0045; A61B 10/02; A61B 10/007; A61B 5/1405
(Continued)

(56) References Cited

U.S. PATENT DOCUMENTS 5,261,416 A * 11/1993 Taussig .............. A61B 10/0045
600/572
5,509,909 A 4/1996 Moy
(Continued)

FOREIGN PATENT DOCUMENTS

| JP | 08052220 | 2/1996 |
|---|---|---|
| WO | 9710749 A1 | 3/1997 |
| WO | 2009098445 A1 | 8/2009 |

OTHER PUBLICATIONS

Notification Concerning Transmittal of International Preliminary Report on Patentability for corresponding patent application No. PCT/EP2011/002325, mailed Nov. 22, 2012, 12 pages.
International Search Report and Written Opinion of the International Searching Authority for corresponding patent application No. PCT/EP2011/002325, dated Nov. 8, 2011, 17 pages.

*Primary Examiner* — Daniel Cerioni
(74) *Attorney, Agent, or Firm* — Shumaker & Sieffert, P.A.

(57) ABSTRACT

The present invention is directed to a method and a device for accurately guiding a chest tube to an intended position within a pleural cavity of an animal or human being. There is also provided a kit-of-parts comprising a catheter and a catheter guiding device according to the present invention.

14 Claims, 22 Drawing Sheets

(51) Int. Cl.
*A61B 17/34* (2006.01)
*A61M 25/06* (2006.01)
*A61B 10/00* (2006.01)
*A61M 25/00* (2006.01)

(52) U.S. Cl.
CPC ..... *A61M 25/0662* (2013.01); *A61M 25/0041* (2013.01); *A61M 25/0069* (2013.01)

(58) Field of Classification Search
USPC .................................................. 600/573, 581
See application file for complete search history.

(56) References Cited

U.S. PATENT DOCUMENTS

| | | |
|---|---|---|
| 5,536,255 A | 7/1996 | Moss |
| 6,270,476 B1* | 8/2001 | Santoianni et al. ........ 604/95.04 |
| 6,592,575 B1 | 7/2003 | Kesten et al. |
| 2002/0032432 A1* | 3/2002 | Nash et al. .................... 604/533 |
| 2002/0052576 A1* | 5/2002 | Massengale ............. 604/164.01 |
| 2005/0021004 A1* | 1/2005 | Cully .................... A61B 18/02 600/585 |
| 2005/0038406 A1* | 2/2005 | Epstein et al. ................ 604/500 |
| 2005/0143690 A1 | 6/2005 | High |
| 2006/0009801 A1 | 1/2006 | McGurk et al. |

* cited by examiner

INSERTING A CLOSED INTERCOSTAL DRAIN

Inserting a closed intercostal drain
State-of-the-art method using blunt technique

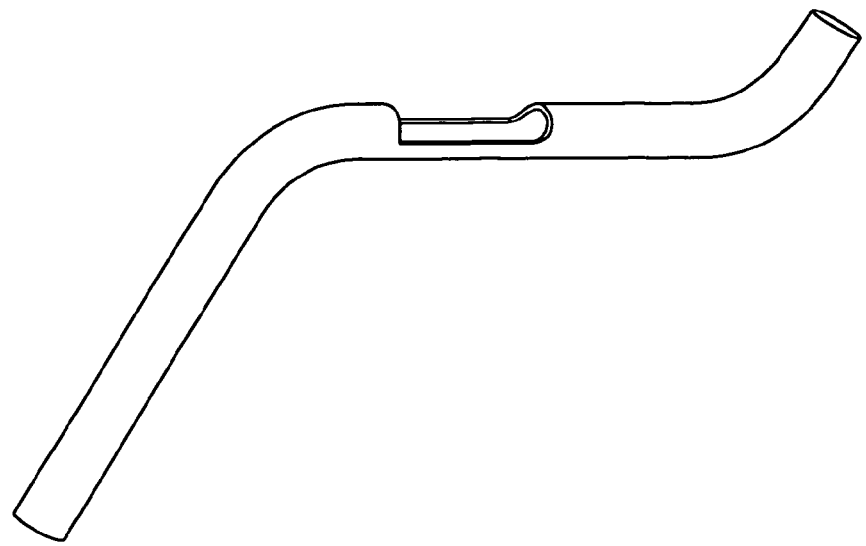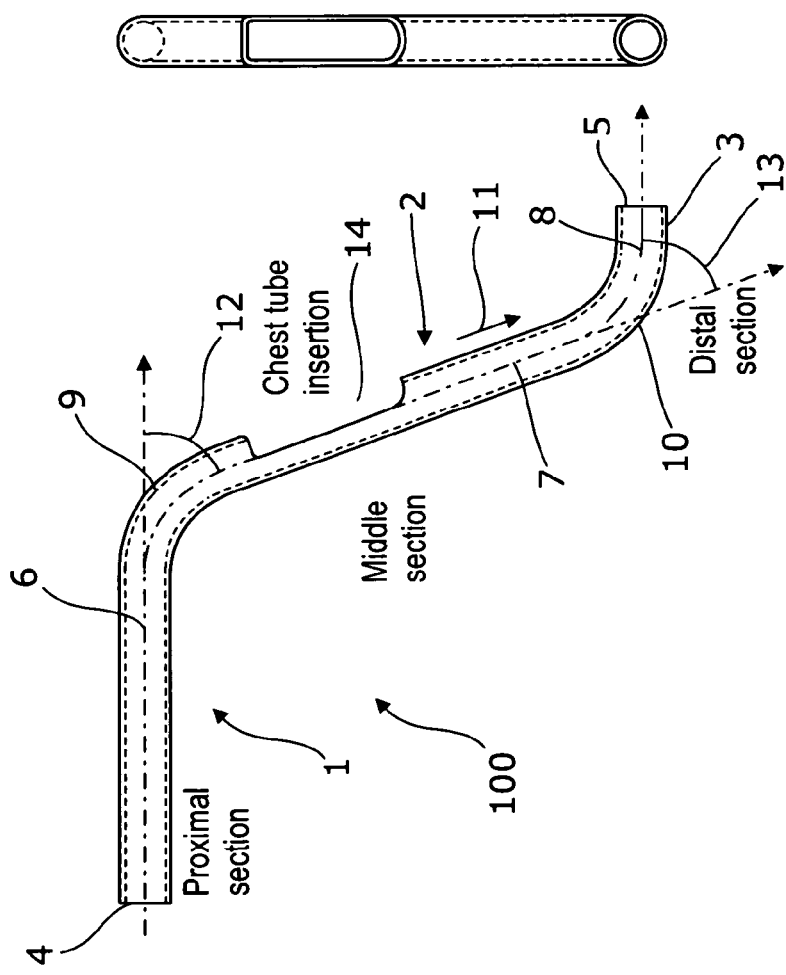
Fig. 3

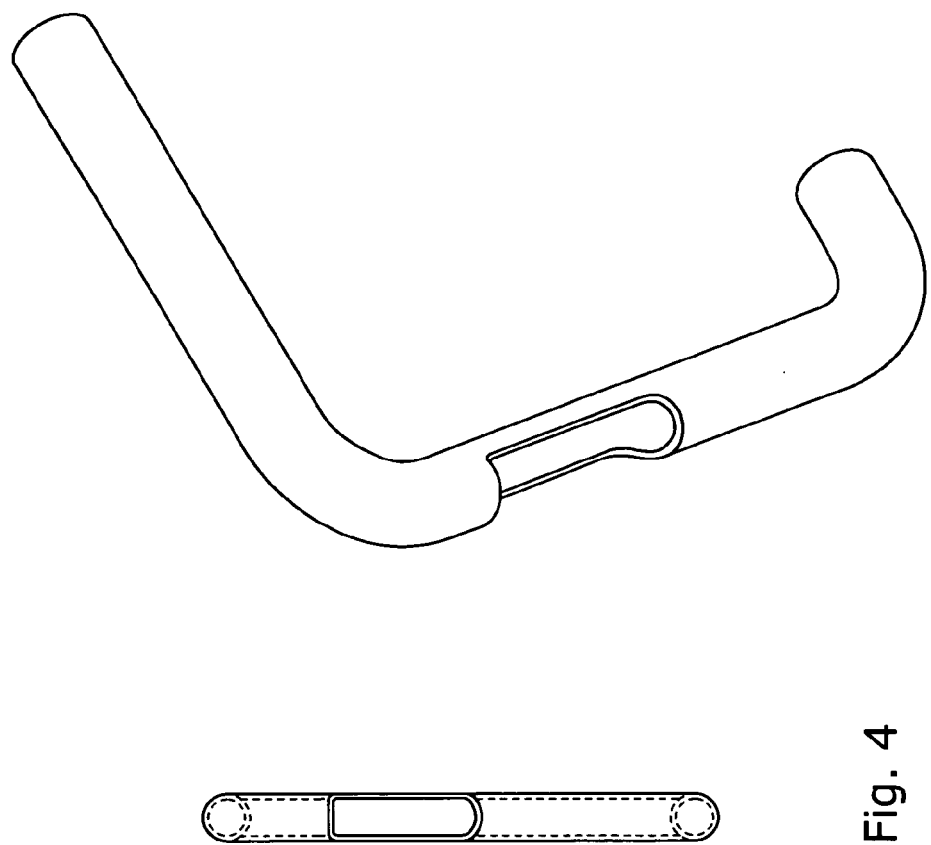
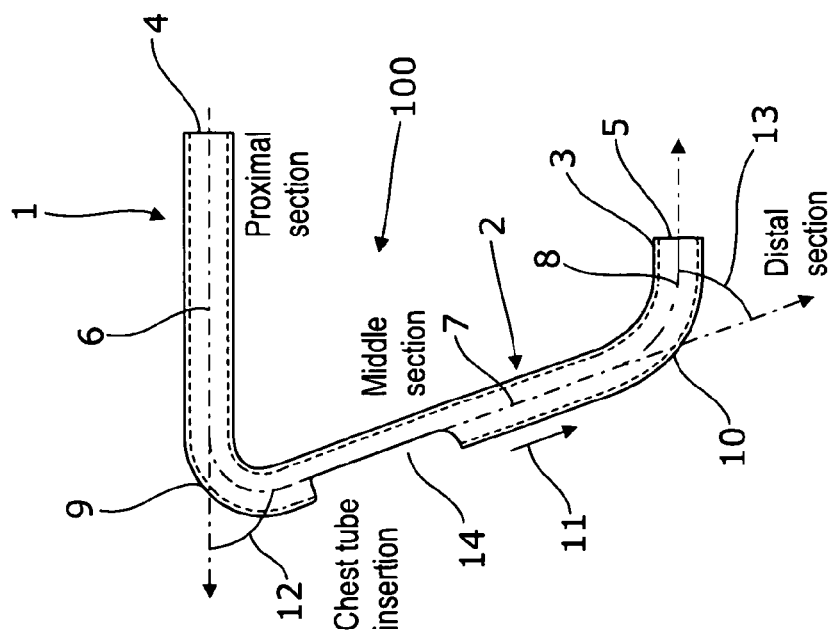
Fig. 4

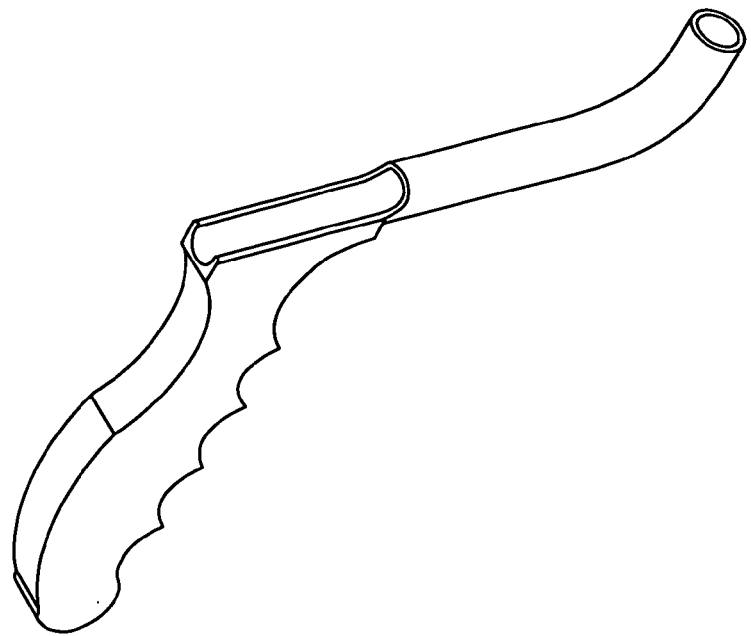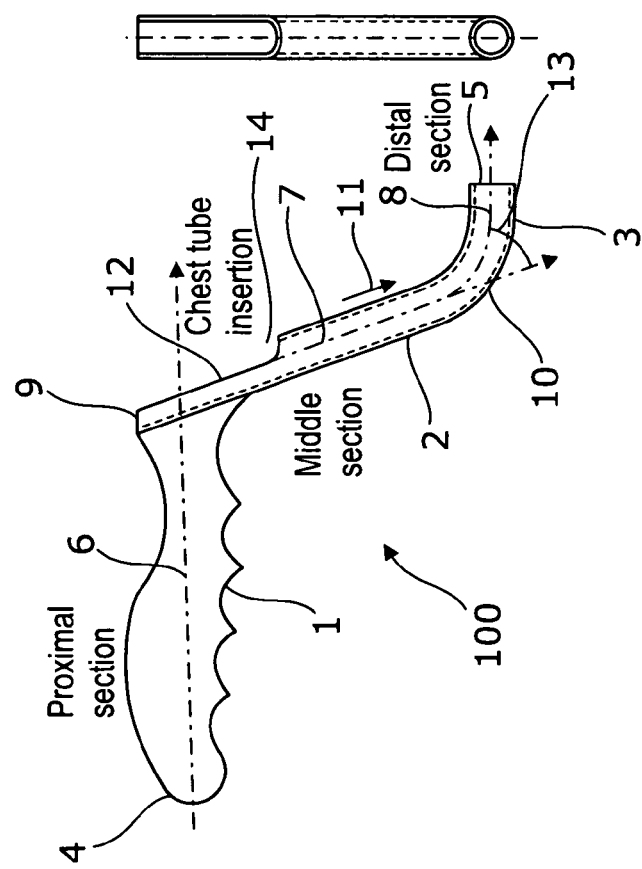
Fig. 6

Fig. 10

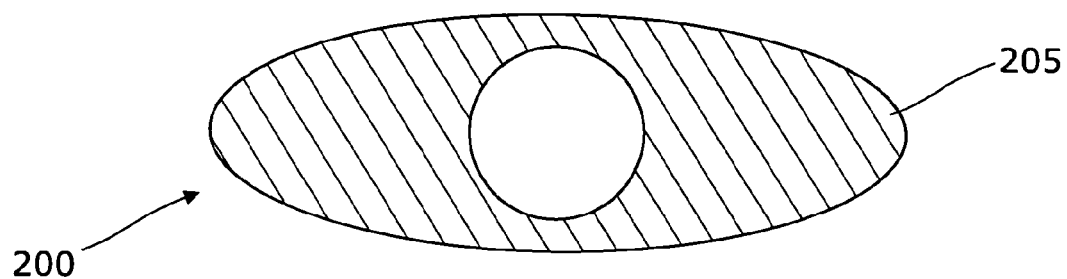
Fig. 11A
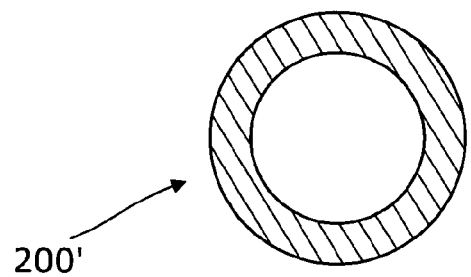
Fig. 11B
Fig. 11

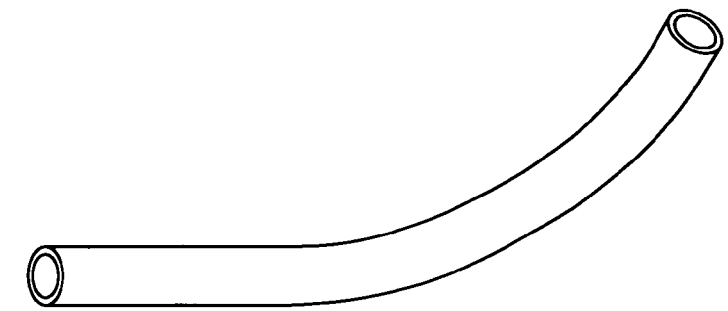
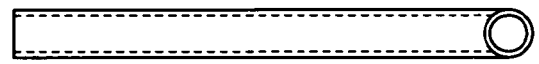
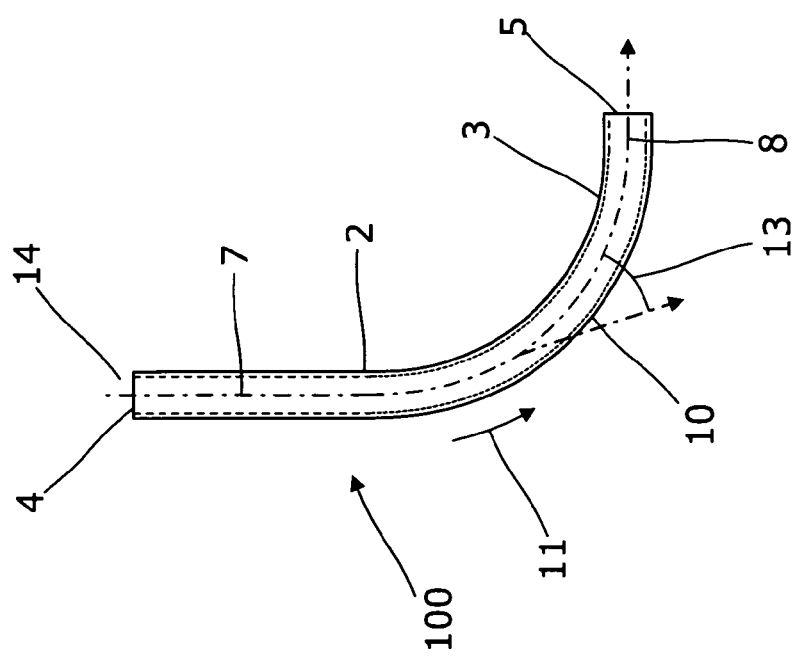
Fig. 12

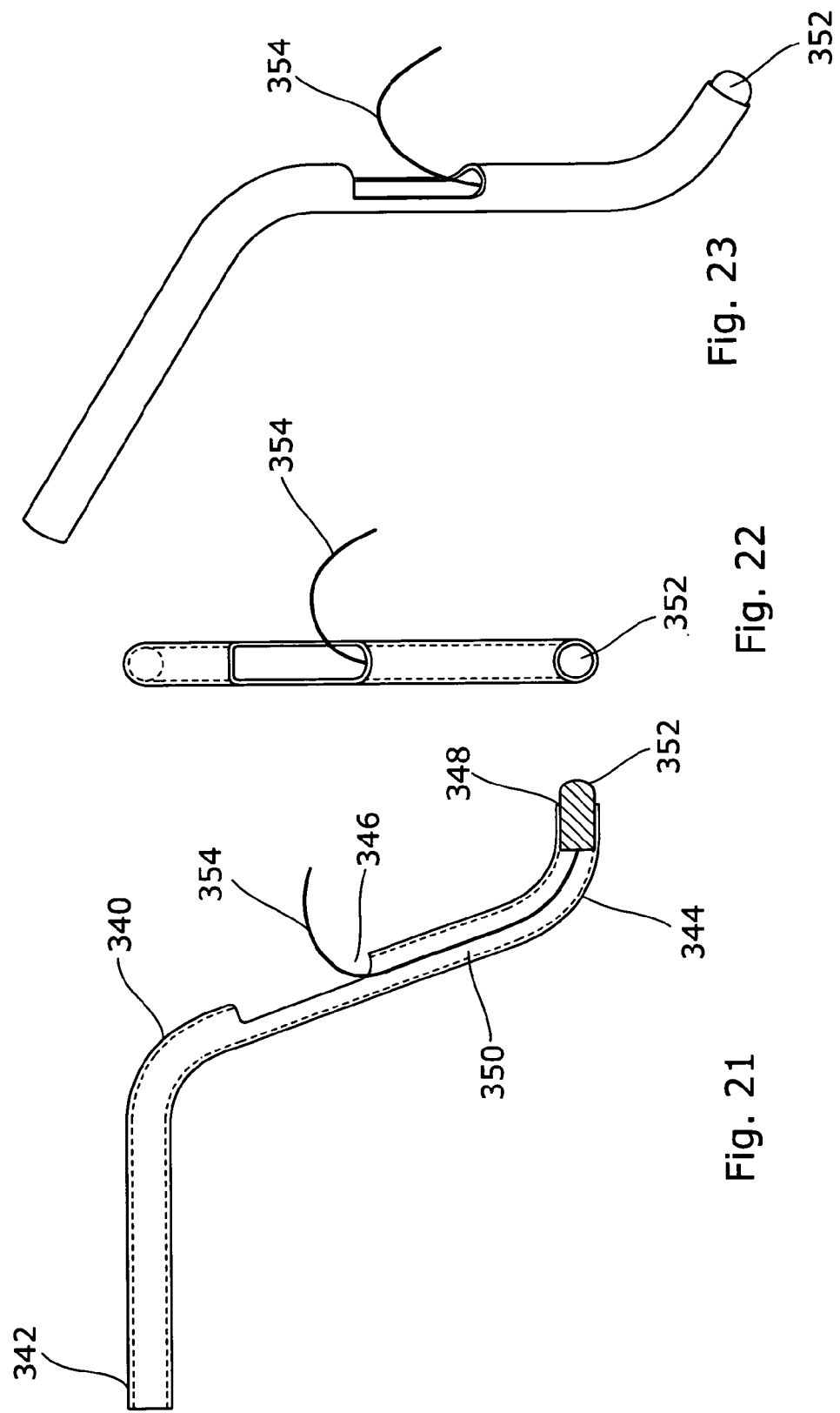

CATHETER GUIDING DEVICE

All patent and non-patent references cited in the present application are hereby incorporated by reference in their entirety.

FIELD OF INVENTION

The present invention is in the field of surgery performed on an animal or human body and employs a catheter guiding device for use in a surgical procedure. The surgical procedure involves the steps of introducing, guiding and accurately positioning a catheter in a body cavity, such as e.g. the pleural cavity, of an individual.

BACKGROUND OF INVENTION

The pleural cavity of a mammal is the body cavity that surrounds the lungs. The pleura is a serous membrane which folds back upon itself to form a two-layered, membrane structure. The thin space between the two pleural layers is known as the pleural cavity.

The outer pleura (parietal pleura) is attached to the chest wall. The inner pleura (visceral pleura) covers the lungs and adjoining structures, including blood vessels, bronchi and nerves.

The pleural cavity, with its associated pleurae, aids optimal functioning of the lungs during respiration. The pleural cavity contains pleural fluid, which allows the pleurae to slide effortlessly against each other during ventilation.

Pleural fluid is a serous fluid produced by the normal pleurae. Most pleural fluid is produced by the parietal circulation (intercostal arteries) and reabsorbed by the lymphatic system. Thus, pleural fluid is produced and reabsorbed continuously under normal physiological conditions.

Individuals experiencing e.g. a pleural effusion (accumulation of fluid in the pleural cavity), hemothorax (accumulation of blood in the pleural cavity), pneumothorax (collapsed lung), or empyema (accumulation of pus in the pleural cavity) often require surgery in the form of insertion of a chest tube into the pleural cavity to provide relief from and/or to treat the observed symptoms.

In case of hydrothorax, hemothorax or chylothorax, the ideal location of the tip of the chest tube is close to the diaphragm, posteriorly in the pleural cavity, since this is the lowest point of the cavity. In case of pneumothorax, the ideal location of the tip of a chest tube is in the cranial, anterior part of the pleural cavity because air tends to be located at the top of the cavity. In case of empyema, the ideal location is into the empyema cavity which can vary in location from patient to patient.

It is absolutely essential that a chest tube is always placed at the intended location of a body cavity. A misplaced chest tube may lead to impaired function which may cause severe discomfort for the patient and furthermore result in an extended hospital admission. A prolonged period of chest tube insertion increases the risk of infection through the chest tube passage. In some cases it is necessary to replace an inserted chest tube and to insert a new chest tube due to an improper and incorrect location of the initially inserted chest tube.

The typical symptoms of pneumonia (lung infection) include fever, cough, and sputum discharge, shortness of breath and chest pain. Pneumonia can progress with parapneumonic effusion and 1-5% of the patients develop pus in the pleural cavity (empyema). This type of lung infection can progress to systemic disease with such signs as weakness, and loss of appetite (anorexia). Chest x rays can allow the clinician to view the pleural effusion or empyema and can also help to detect pneumothorax, since there is visual proof in the displacement of the tissues covering the lungs as a result of air in the pleural cavity. Additionally, during physical examinations, people with pneumothorax have diminished breath sounds, hyperesonance on percussion (a highly resonating sound when the physician taps gently on a patient's back), and diminished ability to expand the chest.

Chest tubes are well known in the art and exist in various shapes and forms, including "straight" as well as "angular" configurations. Chest tubes can be manufactured in rigid as well as flexible polymeric materials and various procedures exist for their insertion into a body cavity.

WO 2006/019783 (Medical Components, Inc.) discloses a catheter tunnelling device integrally connected at one end thereof to a trocar by means of a slidable adapter that facilitates a physical connection between the trocar and the catheter. WO 2006/019783 does not address the problem of how to accurately position a catheter in a body cavity, such as the pleural cavity. Also, use of a trocar is mandatory when operating the catheter tunnelling device. The present invention does not employ a trocar physically connected to a catheter or chest tube.

U.S. Pat. No. 5,509,909 (Moy) discloses a bent chest tube assembly capable of being straightened by a trocar located internally in the chest tube. Once the trocar is retracted from the lumen of the chest tube, the chest tube returns to its pre-formed and fixed, angular shape (angle of approx. 90 degrees). It is disclosed that the bent, distal portion of the chest tube provides an anchoring function and reduces the likelihood of inadvertent removal of the catheter from the pleural cavity. U.S. Pat. No. 5,509,909 does not address the problem of how to accurately position a catheter in a body cavity. Use of a trocar is mandatory when inserting a chest tube in a body cavity according to the method disclosed in U.S. Pat. No. 5,509,909. Also, the present invention does not require or depend on the use of a trocar for directing the insertion of a catheter or chest tube into e.g. a pleural cavity of an individual.

P2005-341987A (Unknown assignee) discloses a curved, trocar guide used for inserting a catheter into a body cavity. P2005-341987A does not address the problem of how to accurately position a catheter in a body cavity, such a the pleural cavity. Use of a trocar is mandatory when inserting a chest tube according to the method disclosed in P2005-341987A. Also, the present invention does not require or depend on the use of a trocar for directing the insertion of a catheter or chest tube into e.g. a pleural cavity of an individual.

U.S. Pat. No. 6,849,061 (Wagner) discloses a bent catheter having a generally, L-shaped form. The catheter material is sufficiently rigid to maintain the distal section of the catheter in a correct position, but flexible enough to move when displaced to prevent further injury to the individual being treated. U.S. Pat. No. 6,849,061 does not address the problem of how to accurately position a catheter in an intended position in a body cavity, such as the pleural cavity of an individual.

U.S. Pat. No. 4,813,929 (Semrad) discloses a method in which a guide wire is inserted into a pleural cavity through a bore needle. A pleural access catheter is delivered to the pleural cavity over the guide wire and a chest tube is subsequently diverted into the pleural cavity through the access catheter. U.S. Pat. No. 4,813,929 does not address the problem of how to accurately position a catheter in an intended position in a body cavity, such as the pleural cavity.

Use of a guide wire is mandatory when inserting a chest tube into a pleural cavity according to the method disclosed in U.S. Pat. No. 4,813,929. Also, the present invention does not require or depend on the use of a guide wire for directing the insertion of a chest tube into e.g. the pleural cavity of an individual.

Use of a trocar is mandatory when using the methods and devices disclosed in WO 2006/019783, U.S. Pat. No. 5,509,909 and P2005-341987A (cf. above). However, the art teaches away from using a trocar for chest tube insertions because of the dangers associated with using a trocar. For example, Klopp et al. states in Dtsch. Med. Wochenschr., 2009, vol. 134(11): pp. 536-9 [PMID: 19235680], that insertion of a chest tube aided by using a trocar frequently results in severe complications such as hemothorax, dislocation, lung lacerations, and injury to organs in the thoracic or abdominal cavity.

As taught in U.S. Pat. No. 4,813,929A (cf. above), a pleural access catheter can be delivered to the pleural cavity over a guide wire and a chest tube can subsequently be diverted into the pleural cavity through an access catheter. While guide wires generally improve the ability to position correctly a chest tube in the pleural cavity of an individual, recent evidence, cf. herein below, suggests that even a guide wire assisted insertion of a chest tube into the pleural cavity does not in all cases result in the correct positioning of the chest tube.

Protic et al. (2009) reported in Eur. J. Emerg. Med. [PMID: 19704377] success rates of a tube thoracostomy study using i) a targeted, wire-guided (TWG) procedure against ii) a classical surgical (CS) procedure. The TWG and CS groups were each divided into four subgroups according to the intended target position of the chest tube in the pleural cavity: back-down-right, front-up-right, front-up-left and back-down-left, respectively. The placement of the chest tube was marked successful if the tip of the chest tube was located at the intended position. The success rate with the TWG procedure was 79%, whereas the success rate with the CS procedure was as low as only 30%.

In summary, it can be concluded that trocars are less safe to use when inserting a chest tube into a pleural cavity. Also, a classical surgical procedure, wherein no directional guidance to aid the correct positioning of a chest tube in the pleural cavity is employed, results in a failure to position a chest tube correctly at the intended position in the pleural cavity in 2 out of 3 patients (cf. 30% success rate, as cited by Protic (2009) herein above).

Although guide wire assisted insertions of chest tubes into the pleural cavity do provide an improved success rate over the classical surgical procedure (cf. above), 1 in 5 patients can nevertheless—based on the study reported by Protic (2009) herein above—be expected to be subjected to unpleasant, inconvenient and unnecessary further surgical steps as a consequence of having had a chest tube incorrectly positioned in the pleural cavity.

Accordingly, there is a need for a simple, inexpensive and safe method for inserting and accurately positioning a chest tube at an intended position in a body cavity, such as e.g. the pleural cavity of an individual.

The unnecessary and additional health care costs associated with a chest tube replacement and an extended hospital admission, the increased risk to a patient of contracting an infection and the pain and general inconvenience caused by the replacement of an incorrectly positioned chest tube can be avoided by using the chest tube guiding device according to the present invention.

SUMMARY OF THE INVENTION

According to the present invention, there is provided a catheter guiding device comprising: a proximal end, a distal end, at least a distal bend or a curved section, and a lumen capable of receiving a catheter; wherein, the lumen comprises at least one catheter entry port and at least one catheter exit port located at the distal end; said at least one catheter entry port and said at least one catheter exit port are separated by the at least a distal bend or a curved section; the catheter device is capable of directing the insertion of the catheter into a body cavity when the catheter exits the catheter exit port, thereby ensuring an accurate positioning of the catheter into the body cavity of an individual at an intended, predetermined position thereof.

Preferably, the catheter comprises or consists of a chest tube.

Conveniently, the body cavity is a pleural cavity of an animal or human body.

Advantageously, the catheter exit port is separated from the catheter entry port by at least one section of the catheter guiding device having a bend or curved section.

Preferably, the curved section is essentially a circular arc.

Conveniently, the bend forms a distal angle, measuring more than 0 degrees but less than 180 degrees.

Advantageously, the device includes a functional relationship between the movement of the proximal end and the distal end.

Preferably, the functional relationship is determined by the measure of distal angle.

Conveniently, the functional relationship is determined by the length of a distal section.

Advantageously, the functional relationship: determines position of the distal end in the body; and defines the direction in which the catheter exits the catheter exit port, the direction being along a distal axis.

Preferably, the distal end is a rounded end.

Conveniently, a part of the distal section is tapered inwards along the direction of the distal axis, from an edge close to the distal end until the distal end.

Advantageously, the edge is a rounded edge.

Preferably, the tapering is gradual over a relatively large distance of distal section, starting from 18 until the distal end 5.

Conveniently, the guiding device further comprises: a proximal section including the proximal end; a mid section including the lumen and the catheter entry port; and a distal section including the distal end and the catheter exit port.

Advantageously, the proximal section forms a proximal angle with the mid section; the distal section forms the distal angle with the mid section, the distal angle defining the distal bend.

Preferably, the device includes a functional relationship between the movement of the proximal end and the distal end.

Conveniently, the functional relationship includes measure of the proximal angle and measure of the distal angle.

Advantageously, the measure of the proximal angle is more than 0 degrees but less than 180 degrees; and the measure of the proximal angle is more than 0 degrees but less than 180 degrees.

Preferably, the proximal angle and the distal angle are selected from a group comprising acute angles, obtuse angles, right angles, and a combination thereof.

Conveniently, the proximal angle and the distal angle are selected from a group comprising a pair of supplementary angles, a pair of complementary angles, and a pair of right angles.

Advantageously, the functional relationship is determined by the length of the distal section.

Preferably, the functional relationship: determines position of the distal end in the body; and defines the direction in which the catheter exits the catheter exit port, the direction being along a distal axis.

Conveniently, the distal portion has a projecting tip to facilitate the insertion of the device into a body cavity.

Advantageously, the projecting tip comprises a lip extending distally from the catheter exit port.

Preferably, the guiding device comprises a removable bung in the lumen at the distal end of the device.

Conveniently, the lumen comprises one or more projections to facilitate the movement of a catheter within the device.

Advantageously, the device is provided with indicia, is coloured and/or is shaped to distinguish between the distal end and the proximal end.

Preferably, the outer wall section is provided with at least one projection to facilitate the accurate positioning of the device into the body cavity.

According to another aspect of the invention, there is provided a two-part guiding device, comprising: a proximal end, a distal end, a lumen capable of receiving a catheter; wherein, the lumen comprises at least one catheter entry port and at least one catheter exit port located at the distal end; and the proximal end, lumen and the distal end are separable in two parts along the axial length of the guiding device.

Preferably, the two-part guiding device further comprises any of the features of the invention listed above in the Summary of the Invention.

Conveniently, the guiding device further comprises a locking means, such as a snap lock, for holding together the two-part of the guiding device together.

Advantageously, the axial length is selected from a group of length of proximal axis, length of mid axis, length of distal axis and a combination thereof.

According to a further aspect of the invention, there is provided a catheter comprising reinforced side walls for preventing or reducing any undesirable sidewards or lateral movement when the catheter is inserted through a catheter guiding device.

According to another aspect of the invention, there is provided a kit-of-parts comprising a catheter, such as a pleural catheter or chest tube, and the catheter guiding device of the invention.

Preferably, the kit-of-parts further comprises a tube stub.

Conveniently, the kit-of-parts is in the form of a sterile, pre-packaged kit-of-parts for single use.

Advantageously, the contents of the kit-of-parts is separated from an external environment by a sterile barrier seal which is broken immediately prior to using the contents of the kit-of-parts in a surgical procedure.

According to another aspect of the invention, there is provided a method for inserting a catheter, such as a pleural catheter, for example a chest tube, into a body cavity of an individual, such as an animal or human being, such as a pleural cavity, during a method of surgery, said surgical method comprising the steps of providing a catheter guiding device of the invention and accurately positioning e.g. a pleural catheter in the pleural cavity of the individual by inserting the pleural catheter into the pleural cavity by using the catheter guiding device according to the present invention.

According to a further aspect of the invention, there is provided a surgical method for improving or ensuring an accurate positioning of a catheter, such as a pleural catheter, in a body cavity, such as a pleural cavity, of an animal or human being, said surgical method comprising the steps of providing a catheter guiding device of the invention and guiding a catheter, such as e.g. a chest tube, into the body cavity, such as a pleural cavity, by inserting the catheter into the body cavity, such as a pleural cavity, by using the catheter guiding device according to the present invention, and accurately directing the catheter to an intended position within the body cavity, such as the pleural cavity.

According to another aspect of the invention, there is provided a method for treating or alleviating the symptoms of an individual, such as an animal or human being, suffering from a clinical condition associated with the pleural cavity, said method of treatment comprising the steps of inserting e.g. a pleural catheter or chest tube into the pleural cavity of the individual to be treated and guiding the insertion of the pleural catheter by using the methods of the invention for accurately directing a catheter to an intended position of a body cavity, such as a pleural cavity.

According to a further aspect of the invention, there is provided a method for diagnosing e.g. an infection and/or a malignancy within the pleural cavity, said method comprising the steps of inserting a pleural catheter or chest tube into the pleural cavity of the individual, such as an animal or human being, by using the methods of the invention for accurately directing a catheter to an intended position within the pleural cavity, collecting a fluid sample from the pleural cavity of the individual by draining at least part of said pleural cavity with said catheter, analysing ex vivo said fluid sample, and diagnosing said infection and/or said malignancy based on the result of said ex vivo analysis.

According to another aspect of the invention, there is provided a catheter guiding device of the invention for use in a method for treating or alleviating the symptoms of an individual, such as an animal or human being, suffering from a clinical indication associated with the pleural cavity, said method comprising the steps of inserting a pleural catheter into the pleural cavity of the individual and guiding the insertion of the catheter by using the methods of the invention for accurately directing a pleural catheter to an intended position within the pleural cavity.

Preferably, the method further comprises the step of removing air, blood, pus, fluids and/or chylos from the pleural cavity.

According to a further aspect of the invention, there is provided a catheter guiding device for use in a method for diagnosing an infection and/or a malignancy within the pleural cavity, said method comprising the steps of inserting a catheter or chest tube into the pleural cavity of the individual, such as an animal or human being, by using the methods of the invention for accurately directing a catheter to an intended position within the pleural cavity, collecting a fluid sample from the pleural cavity of the individual by draining at least part of said pleural cavity with said catheter, analysing ex vivo said fluid sample, and diagnosing said infection and/or malignancy based on the result of said ex vivo analysis.

According to another aspect of the invention, there is provided the use of a catheter guiding device of the invention in the manufacture of a kit-of-parts further comprising a catheter, said kit-of-parts being for use in a method for treating or alleviating the symptoms of an individual, such as an animal or human being, suffering from a clinical indication associated with the pleural cavity, said method comprising the steps of inserting a pleural catheter into the pleural cavity of the individual and guiding the insertion of the catheter by using the methods of the invention for accurately directing a pleural catheter to an intended position within the pleural cavity.

According to a further aspect of the invention, there is provided the use of a catheter guiding device of the invention in the manufacture of a kit-of-parts further comprising a catheter, said kit-of-parts being for use in a method for diagnosing an infection and/or a malignancy within the pleural cavity, said method comprising the steps of inserting the catheter into the pleural cavity of the individual, such as an animal or human being, by using the methods of the invention for accurately directing a catheter to an intended position within the pleural cavity, collecting a fluid sample from the pleural cavity of the individual by draining at least part of said pleural cavity with said catheter, analysing ex vivo said fluid sample, and diagnosing said infection and/or malignancy based on the result of said ex vivo analysis.

The present invention is directed to a method and a device for accurately guiding a chest tube to an intended position within a pleural cavity of an animal or human being. There is also provided a kit-of-parts comprising a catheter and a catheter guiding device according to the present invention.

Chest tubes can in principle be inserted by using one of three different techniques: 1) Ultrasonic guided technique 2) Trocar guided technique 3) Blunt dissection technique.

Chest tube insertion using the blunt dissection technique is today a "blind" procedure as explained in more detail herein below. The present invention remedies the "blindness" of the conventional blunt dissection technique.

Conventional, state-of-the-art chest tube insertion using the blunt dissection technique can be performed by carrying out the following steps: 1) Disinfection and local anaesthesia in the skin in the 5th intercostal space anterior to the mid axillary line (the safe area). 2) Incision of the skin 3) Blunt dissection using a forceps through the thoracic wall to the pleural cavity. 4) A finger is inserted through the passage to verify that the pleural cavity has been entered. 5) The tip of the chest tube is clamped with a curved forceps and inserted into the chest cavity. 6) The curved forceps holding the tip of the chest tube is pointed in the intended direction. 7) The clamp is released and the chest tube is advanced to the optimal dept. 8) The chest tube is sutured to the skin to prevent it from falling out. 9) Once the chest tube is in place a chest x-ray is taken to check the location of the drain.

The procedure is a "blind" procedure as the medical practitioner does not have the ability to accurately direct and accurately position the chest tube in a pleural cavity using the state-of-the art blunt dissection technique. When advancing the chest tube into the pleural cavity, the tip of the chest tube is no longer visible and hence it may be malpositioned. Accordingly, using the state-of-the art blunt dissection technique there is a serious risk of mal-positioning of the chest tube as also disclosed herein above.

Following release of the clamp (cf. step 7 above), the direction in which the chest tube is advanced is in principle not guided and any advancement of the chest tube is assisted only by a medical practitioner holding on to the part of the chest tube which is located outside the patient.

During advancement of the chest tube using the state-of-the art blunt dissection technique, the chest tube may be inadvertently positioned on the outer side of pleura parietale, interfissural or even intraparenchymal (perforate the lung) if the direction of the insertion of the chest tube inside the chest cavity is pointing in the direction of the lung.

Furthermore, insertion of chest tubes is often one of the first procedures performed by young, less experienced thoracic surgeons and trauma surgeons, and the procedure is often an acute procedure performed under stress and with severe time constraints.

Also, an accurate positioning of a chest tube is more difficult to achieve in obese patients and in patients which have e.g. profuse subcutaneous emphysema, large mammae, or if the patient is agitated, frightened or panic stricken. The procedure associated with inserting a chest tube is far from always easy to carry out.

The catheter guiding device according to the present invention aids the medical practitioner in correctly positioning a chest tube under often difficult circumstances.

Accordingly, one aspect of the present invention provides a catheter guiding device suitable for accurately inserting a catheter into a body cavity of an individual at an intended, predetermined position thereof. The catheter can be a chest tube of a suitable diameter and the body cavity can be a pleural cavity of an animal or human body.

The catheter guiding device comprises a lumen into which a catheter can be inserted through a first opening, or catheter entry port, of the catheter guiding device. A second opening, or catheter exit port, is preferably located at a distal end of the catheter guiding device. The catheter exit port is separated from the catheter entry port by at least one section of the catheter guiding device having a bent or curved shape or form, such as e.g. essentially the form of a circle arc. The exact form of the bent or curved section of the guiding device is not essential as long as the catheter can be advanced through the lumen under practical circumstances without a "kink" being generated in the catheter.

It is important for the functionality of the catheter guiding device according to one embodiment of the present invention that at least one curved section is located in the distal end of the device, which is located in a body cavity during use of the catheter guiding device, so that a movement, including a rotation, of the proximal end of the catheter guiding device, which is located outside the patient to be treated, by a medical practitioner during a method of surgery, will result in the positioning of the exit port of the catheter guiding device in a position which defines an intended axial exit direction of the catheter once the catheter exits the exit port of the catheter guiding device. The ability of being able to define an intended, axial exit direction of the catheter once the catheter exits the exit port of the catheter guiding device is a requirement for the medical practitioner to be able to direct the catheter accurately into a body cavity, such as a pleural cavity, in order to accurately locate the catheter therein at an intended location.

A device not having a substantially curved section located in the distal end thereof, i.e. the end of the device which is located in a body cavity during use of the catheter guiding device, does not allow the medical practitioner, under practical circumstances, to define in all cases an intended axial exit direction of the catheter which enables the medical practitioner to accurately position a catheter in a body cavity of a patient during a method of surgery. The reason being that an essentially straight exit port section of the catheter guiding device will restrict and limit the angle at which the exit port can be positioned in a body cavity once the catheter guiding device is entered into the body cavity during a surgical method. The rotation of a catheter guiding device having an essentially straight exit port section does not allow a medical practitioner to point the exit port of the device in all desirable directions once the catheter guiding device has been entered into a body cavity during a surgical procedure.

Accordingly, it is the curved section of the distal end of the catheter guiding device which ensures—when a medical practitioner operates, i.e. moves and/or rotates, the catheter guiding device during use thereof and positions the distal opening of the device in an intended position defining an intended, axial exit direction of the catheter that a catheter can exit the distal end of the catheter guiding device located in a body cavity in a direction which is intended and required for being able to accurately position the catheter, such as a chest tube, at an intended position of a body cavity, such as a pleural cavity.

The at least one curved section of the catheter guiding device located in the distal end of the catheter guiding device can be operably connected to other parts of the catheter guiding device. In one embodiment, the at least one curved section of the catheter guiding device located in the distal end of the device operably connects the first and second openings of the device, optionally in combination with other guide sections having other shapes and forms as required for the design of the catheter guiding device, including guide sections having curved sections, such as arc formed shapes, as well as guide sections being at least essentially straight, i.e. non-angular in shape.

The catheter exit port located in the extreme distal end of the guiding device can have a tapering end so as to facilitate entry of the catheter into the incision of the skin while preferably retaining a uniform, internal diameter of the lumen of the guiding device.

The guiding device can comprise a collar with a diameter significantly larger than the diameter of the tube of the guiding device. The functional of the collar is to prevent the guiding device from being entered too far into the body cavity of an individual under practical circumstances. The position of the collar on the guiding device will typically be somewhere between the distal, bent or curved section and a middle or proximal section of the guiding device. The collar should not limit the movement of the extreme distal end of the guiding device, but merely ensure that the guiding device, once suitably inserted into the body cavity of an individual, remains in place at a fixed position without the risk of being inserted too far into the body cavity.

In another aspect the present invention provides a kit-of-parts comprising a catheter, such as a pleural catheter or chest tube, and a catheter guiding device according to the present invention and optionally also a tube stub. The kit-of-parts is preferably a sterile, pre-packaged kit-of-parts for single use only. The contents of the kit-of-parts can be separated from an external environment by a sterile barrier seal which is broken immediately prior to using the contents of the kit-of-parts in a surgical procedure.

The kit-of-parts can be for emergency use and e.g. further comprise one or more of a scalpel, a needle and sutures, a pair of surgical scissors, a clamp, a disinfectant, anaesthetica, cover, gaze, dressings, and a suction device and/or a collection bag with a one way valve capable of being operably connected to the catheter during use thereof. The kit-of-parts may comprise multiple catheters of different sizes and/or one or more catheter guiding device(s) capable of being operably used in combination with said catheters of different sizes.

In yet another aspect the present invention provides a method for inserting a catheter, such as a pleural catheter, into a body cavity of an individual, such as an animal or human being, such as a pleural cavity, during a method of surgery, said surgical method comprising the steps of providing a catheter guiding device according to the present invention, and accurately positioning e.g. a pleural catheter in the pleural cavity of the individual by inserting the pleural catheter into the pleural cavity by using the catheter guiding device according to the present invention.

In a further aspect the present invention provides a surgical method for improving or ensuring an accurate positioning of a catheter, such as a pleural catheter, in a body cavity, such as a pleural cavity, of an animal or human being, said surgical method comprising the steps of providing a catheter guiding device according to the present invention, and guiding a catheter, such as e.g. a chest tube, into the body cavity, such as a pleural cavity, by inserting the catheter into the body cavity, such as a pleural cavity, by using the catheter guiding device according to the present invention, and accurately directing the catheter to an intended position within the body cavity, such as the pleural cavity.

In a still further aspect the present invention provides a method for treating or alleviating the symptoms of an individual, such as an animal or human being, suffering from a clinical condition associated with the pleural cavity, said method of treatment comprising the steps of inserting e.g. a pleural catheter or chest tube into the pleural cavity of the individual to be treated and guiding the insertion of the pleural catheter by using the methods of the present invention for accurately directing a catheter to an intended position of a body cavity, such as a pleural cavity.

In an even further aspect the present invention provides a method for diagnosing e.g. an infection and/or a malignancy within the pleural cavity, said method comprising the steps of inserting a pleural catheter or chest tube into the pleural cavity of the individual, such as an animal or human being, by using the methods of the present invention for accurately directing a catheter to an intended position within the pleural cavity, collecting a fluid sample from the pleural cavity of the individual by draining at least part of said pleural cavity with said catheter, analysing ex vivo said fluid sample, and diagnosing said infection and/or said malignancy based on the result of said ex vivo analysis.

In a yet further aspect the present invention provides a catheter guiding device for use in a method for treating or alleviating the symptoms of an individual, such as an animal or human being, suffering from a clinical indication associated with the pleural cavity, said method comprising the steps of inserting a pleural catheter into the pleural cavity of the individual and guiding the insertion of the catheter by using the methods of the present invention for accurately directing a pleural catheter to an intended position within the pleural cavity.

In an even further aspect the present invention provides a catheter guiding device for use in a method for diagnosing an infection and/or a malignancy within the pleural cavity, said method comprising the steps of inserting a catheter or chest tube into the pleural cavity of the individual, such as an animal or human being, by using the methods of the present invention for accurately directing a catheter to an intended position within the pleural cavity, collecting a fluid sample from the pleural cavity of the individual by draining at least part of said pleural cavity with said catheter, analysing ex vivo said fluid sample, and diagnosing said infection and/or malignancy based on the result of said ex vivo analysis.

In a yet further aspect the present invention provides the use of a catheter guiding device in the manufacture of a kit-of-parts further comprising a catheter, said kit-of-parts being for use in a method for treating or alleviating the symptoms of an individual, such as an animal or human being, suffering from a clinical indication associated with the pleural cavity, said method comprising the steps of inserting a pleural catheter into the pleural cavity of the individual and guiding the insertion of the catheter by using the methods of the present invention for accurately directing a pleural catheter to an intended position within the pleural cavity.

In a yet further aspect the present invention provides the use of a catheter guiding device in the manufacture of a kit-of-parts further comprising a catheter, said kit-of-parts being for use in a method for diagnosing an infection and/or a malignancy within the pleural cavity, said method comprising the steps of inserting the catheter into the pleural cavity of the individual, such as an animal or human being, by using the methods of the present invention for accurately directing a catheter to an intended position within the pleural cavity, collecting a fluid sample from the pleural cavity of the individual by draining at least part of said pleural cavity with said catheter, analysing ex vivo said fluid sample, and diagnosing said infection and/or malignancy based on the result of said ex vivo analysis.

DEFINITIONS

Atmospheric pressure: The force exerted by air at any point on the earth's surface. Mean atmospheric pressure at sea level is approximately 1,000 millibars (100 kilopascals).

Catheter: A tube, such as a chest tube, capable of being placed within a body cavity of an individual, such as a human being. When placed in the thoracic cavity, such as a pleural cavity, the chest tube can be used for removing trapped air and/or fluid from this cavity and thereby provide relief from clinical indications such as e.g. pneumothorax and/or pleural effusions resulting from accumulation of air and/or fluids within the thoracic cavity. Pleural effusion drainage can also allow a collapsed lung to re-expand, thereby ensuring that the lung can function normally. The term catheter is used interchangeably with chest tube herein.

Chest tube: See catheter herein above.

Empyema: Accumulation of pus in the pleural space.

Hemothorax: Accumulation of blood in the pleural cavity, usually caused by a chest injury.

Intrapleural: Situated between the parietal pleura and the visceral pleura within the pleural cavity Pleura: Thin membrane that covers each half of the thorax, surrounding and protecting the lung on that side.

Pleural cavity: The space within each pleura, which contains the lungs.

Pleural effusion: Fluid in the pleural cavity, caused by, among other things, congestive heart failure, cancer, tuberculosis, and lung infections.

Pneumothorax: Accumulation of air in the pleural cavity, which causes the lung to collapse. Causes include, among others, lung disease, penetrating trauma, and certain medical procedures, including ventilation and cardiopulmonary resuscitation, pacemaker implantation, CT-guidet needle aspiration of tumours in the lung, insertion of a central venous catheter.

Proximal end (4): defines the end of the guiding device 100 closer and accessible to the medical practitioner when the guiding device 100 is in use. In other words, it is the end which is farther away from the desired position of the body cavity, when the device 100 is in use.

Distal end (5): defines the end of the guiding device 100 farther away from the medical practitioner when the guiding device 100 is in use. In other words, it is the end which is closer to the desired position of the body cavity, when the device 100 is in use, and includes the catheter exit port.

Proximal section (1): In an embodiment of the invention, the proximal section 1 defines a part of the device closer and accessible to the medical practitioner when the guiding device 100 is in use. In other words, it is the section which is farther away from the desired position in the body, when the device 100 is in use. Typically, the proximal section 1 therefore, includes the proximal end 4. In another embodiment of the invention, the guiding device may not include the proximal section 1 and in this case, a part of a mid section may be considered as the proximal section for understanding purposes (see FIG. 12).

Distal section (3): defines a part of the device 100 farther away from the medical practitioner when the guiding device 100 is in use. In other words, it is the section which is closer to the desired position in the body, when the device 100 is in use. The distal section 3 includes the distal end 5, which includes the catheter exit port.

Mid section (2): In an embodiment of the invention, the mid section 2 defines a part of the device connecting the proximal section 1 and the distal section 5.

In another embodiment of the invention, where the device does not include the proximal section, the mid section includes the proximal end 4 (see FIG. 12). Person skilled in the art would appreciate that in such situations, a small part of the mid section 2 including and near the proximal end 4 may be considered as a proximal section for understanding purposes and therefore, complies with the requirement that the proximal end is closer and accessible to the medical practitioner when the guiding device 100 is in use. However, the proximal axis and the mid axis would be the same.

The mid section 2 includes the entry port 14 for allowing the catheter to be introduced in the guiding device 100.

Proximal axis (6): Axis along the length of the proximal section 1 and forms a proximal angle 12 with a mid axis 7. The direction of the proximal axis 6 along the movement (11) of catheter in the guiding device 100 is represented by extended direction of the proximal axis 6.

Distal axis (8): Axis along the length of the distal section 3 and forms a distal angle 13 with a mid axis 7. The direction of the distal axis 8 complying with the movement 11 of catheter in the guiding device 100 is represented by extended direction of the distal axis 8. In one embodiment, the direction of the distal axis 8 is opposite to the direction of the proximal axis 6 (FIG. 4). However, in another embodiment, the direction of the distal axis 8 may be in the same direction to that of the proximal axis (FIG. 3). Person skilled in the art would appreciate that the directions of the proximal axis and the distal axis are not limited to the previous two embodiments because the proximal axis and the distal axis may form other angles between each other as well.

Mid axis (7): Axis along the length of the mid section 2 and forms a proximal angle 12 with the proximal axis 6 and a distal angle 13 with the distal axis 8 respectively. The direction of the mid axis 7 complying with the movement 11 of the catheter in the guiding device 100 is represented by extended direction of the mid axis 7.

Proximal angle (12): Angle formed between the proximal axis 6 and mid axis 7 at a proximal bend 9. The proximal angle 12 is measured between the direction of the proximal axis 6 and direction of the mid axis 7 such that the direction of these axes comply with movement 11 of the catheter in the guiding device, as represented in the accompanying figures.

Distal angle (13): Angle formed between the distal axis 8 and mid axis 7 at a distal bend 10. The distal angle 12 is measured between the direction of the distal axis 8 and direction of the mid axis 7 such that the direction of these axes comply with the movement 11 of the catheter in the guiding device, as represented in the accompanying figures.

Proximal bend (9): Bend formed in the guiding device 100 between the proximal section 1 (defined by proximal axis 6) and mid section 12 (defined by mid axis 7) because of the proximal angle 12.

Distal bend (10): Bend formed in the guiding device 100 between the distal section 3 (defined by distal axis 8) and mid section 2 (defined by mid axis 7) because of the distal angle 13.

BRIEF DESCRIPTION OF THE DRAWINGS

The embodiments of the invention, together with its advantages, may be best understood from the following detailed description taken in conjunction with the accompanying figures where same features are represented by same numerals.

FIG. 3 illustrates an embodiment of the catheter guiding device 100 having a proximal section 1 and a distal section 3 separated by a mid section 2 comprising an entry port 14 for the insertion of a chest tube. The handle portion, which may be understood as the proximal section 1, of the device is positioned at the proximal end 4 of the device and defines proximal axis 6 having a proximal direction as represented in the figure. The distal section 3 and the mid section 3, defined by their respective distal axis 8 and mid axis 7, form a distal angle 13 defining a distal bend 10. Similarly, the proximal section 1 and the mid section 3, defined by their respective proximal axis 6 and mid axis 7, form a proximal angle 12 defining a proximal bend 9. The proximal angle 12 and the distal angle 13 share a relation defining a functional relationship between the movement of the distal end 4 and the proximal end 5. The chest tube enters the lumen of the guiding device through the entry port 14 as illustrated and is diverted through the lumen, defined between the entry port 14 and the exit port at the distal point 5, of the guiding device by a medical practitioner and exits the guiding device at the distal end thereof in a direction of the distal axis. In some embodiments, the direction of exit of the chest tube is at least essentially similar to the proximal axis direction. However, in other embodiments, the direction of exit of the chest tube is not essentially parallel to that of the direction of the proximal axis.

Figure 1:
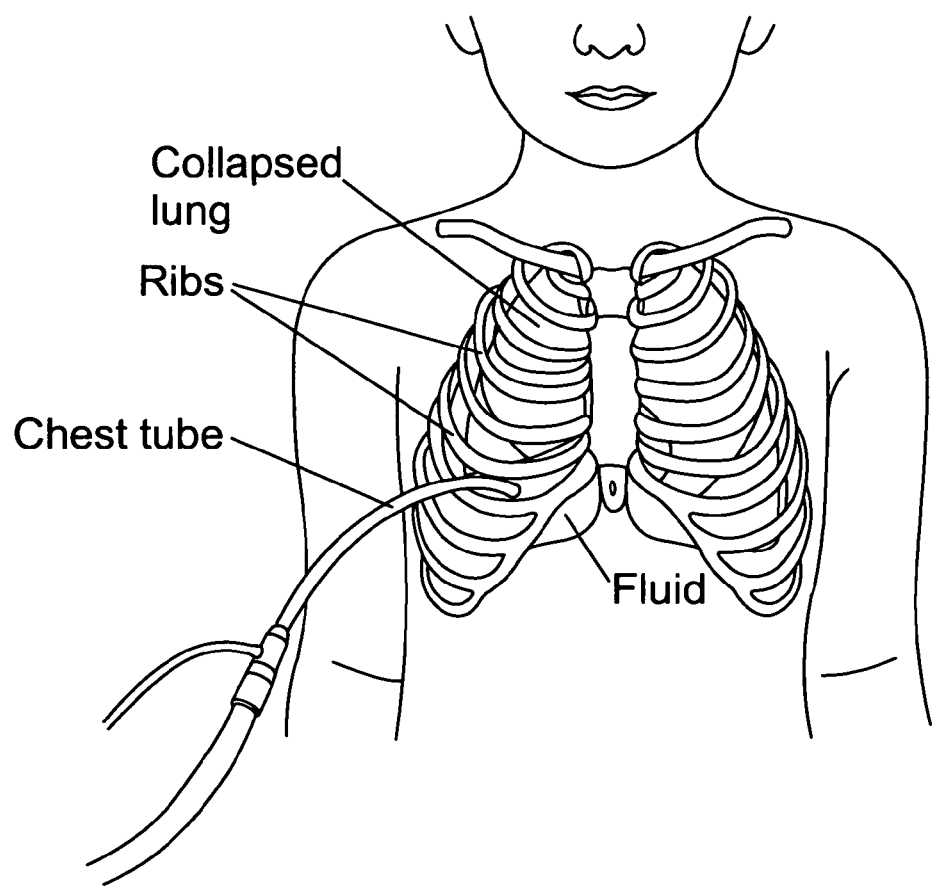
FIG. 1 illustrates an individual suffering from pneumothorax (collapsed lung) and in need of having fluid removed from the pleural cavity. A chest tube is inserted into the pleural cavity through an incision in the intercostal space between two ribs.
Figure 2A:
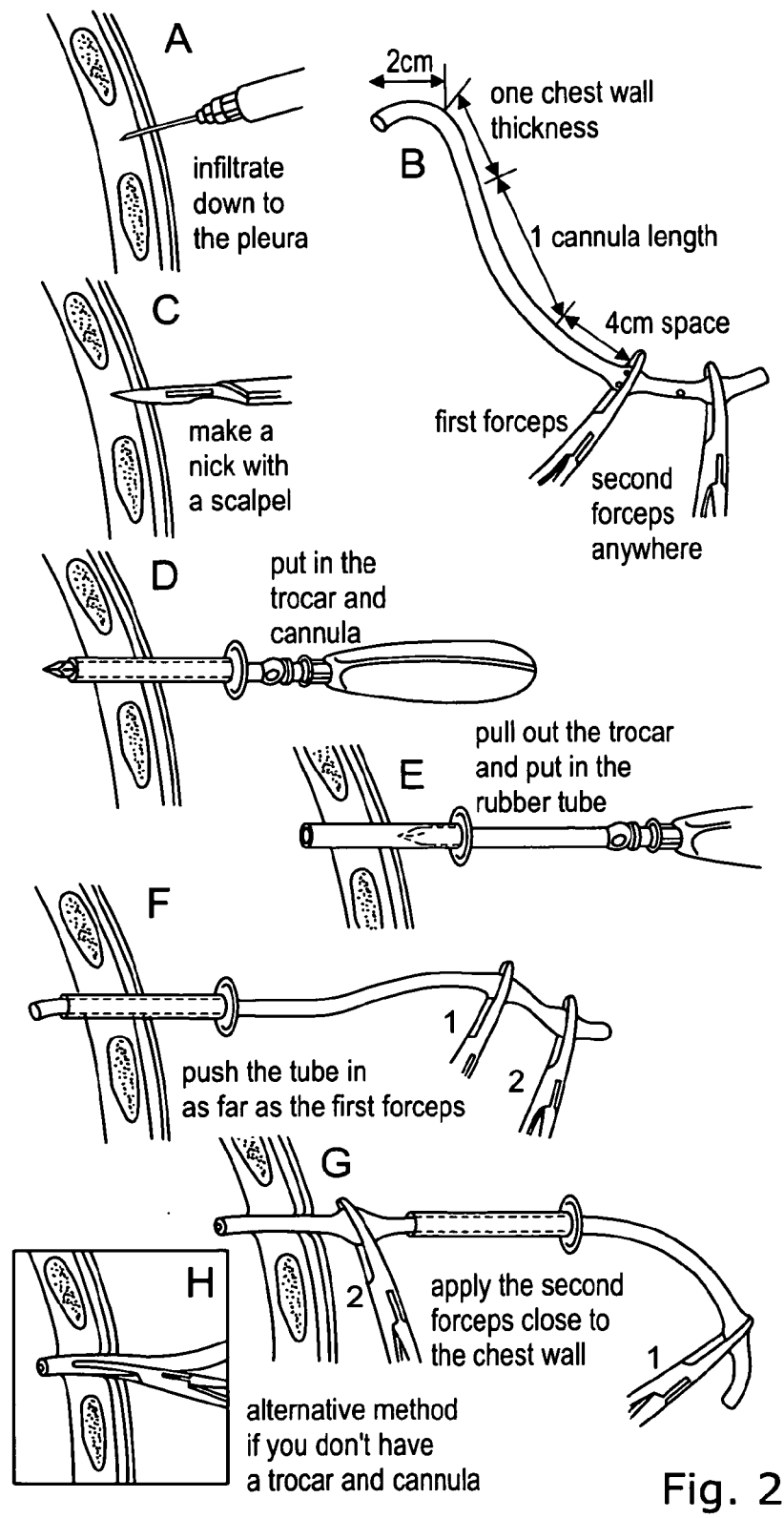
FIG. 2A illustrates various state-of-the-art methods available to a medical practitioner when inserting a chest tube into the pleural cavity. Panel A illustrates an infiltrate down to the pleura. Panel B illustrates a chest tube attached to two forceps used for inserting the chest tube into the pleural cavity. Panel C illustrates a scalpel used for making an incision into the intercostal space between two ribs. Panel D. illustrates a trocar used for inserting a cannula into an incision in the intercostal space. Panel E illustrates the excision of the trocar from the cannula. Panel F illustrates a chest tube having been inserted into the cannula by means of two forceps. Panel G illustrates the removal of the cannula following insertion of the chest tube into the pleural cavity. Panel H illustrates an alternative method whereby a chest tube can be inserted into the pleural cavity.
Figure 2B:
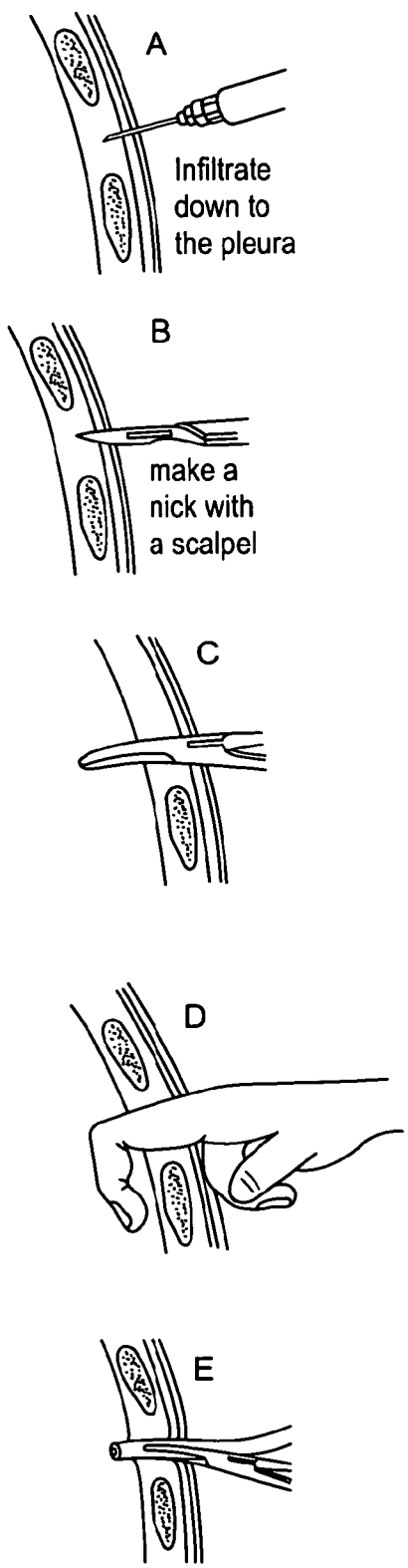
FIG. 2B illustrates state-of-the-art method available to a medical practitioner when inserting a chest tube into the pleural cavity. Panel A illustrates an analgetic infiltrate down to the pleura. Panel B illustrates a scalpel used for making a skin incision into the intercostal space between two ribs. Panel C illustrates a blunt technique with a scalpel for penetrating into the pleural cavity. Panel D illustrating that a finger is inserted through the passage to verify that the pleural cavity has been entered. Panel E illustrating the tip of the chest tube is clamped with a curved forceps and inserted into the chest cavity.

By observing the relationship between the directions of proximal axis and distal axis, as defined by the proximal angle and distal angle, relative movement of the distal end with respect to the proximal end may be determined and thus, the medical practitioner will be able to ascertain the direction in which the chest tube is inserted into the pleural cavity.

FIG. 4 illustrates an embodiment of the catheter guiding device 100 having a proximal section 1 and a distal section 3 separated by a mid section 2 comprising an entry port 14 for the insertion of a chest tube. The handle portion, which may be understood as the proximal section 1, of the device is positioned at the proximal end 4 of the device 100 and defines a proximal axis 6 having a proximal direction as represented in the figure. The chest tube enters the lumen, defined between the entry port 14 and the exit port at the distal end 5, of the guiding device through the entry port 14 as illustrated and is diverted through the lumen at the distal bend 10 of the guiding device by a medical practitioner and the chest tube exits the guiding device at the distal end thereof in a direction of the distal axis 8. In the shown embodiment, the direction of exit of the chest tube is at least essentially opposite to the direction of the proximal axis 6. However, in other embodiments, the direction of exit of the chest tube is not essentially anti-parallel to that of the direction of the proximal axis.

By observing the relationship between the directions of proximal axis 6 and distal axis 8, as defined by the proximal angle 12 and distal angle 13, relative movement of the distal end with respect to the proximal end may be determined and thus, the medical practitioner will be able to ascertain the direction in which the chest tube is inserted into the pleural cavity.

Figure 5:
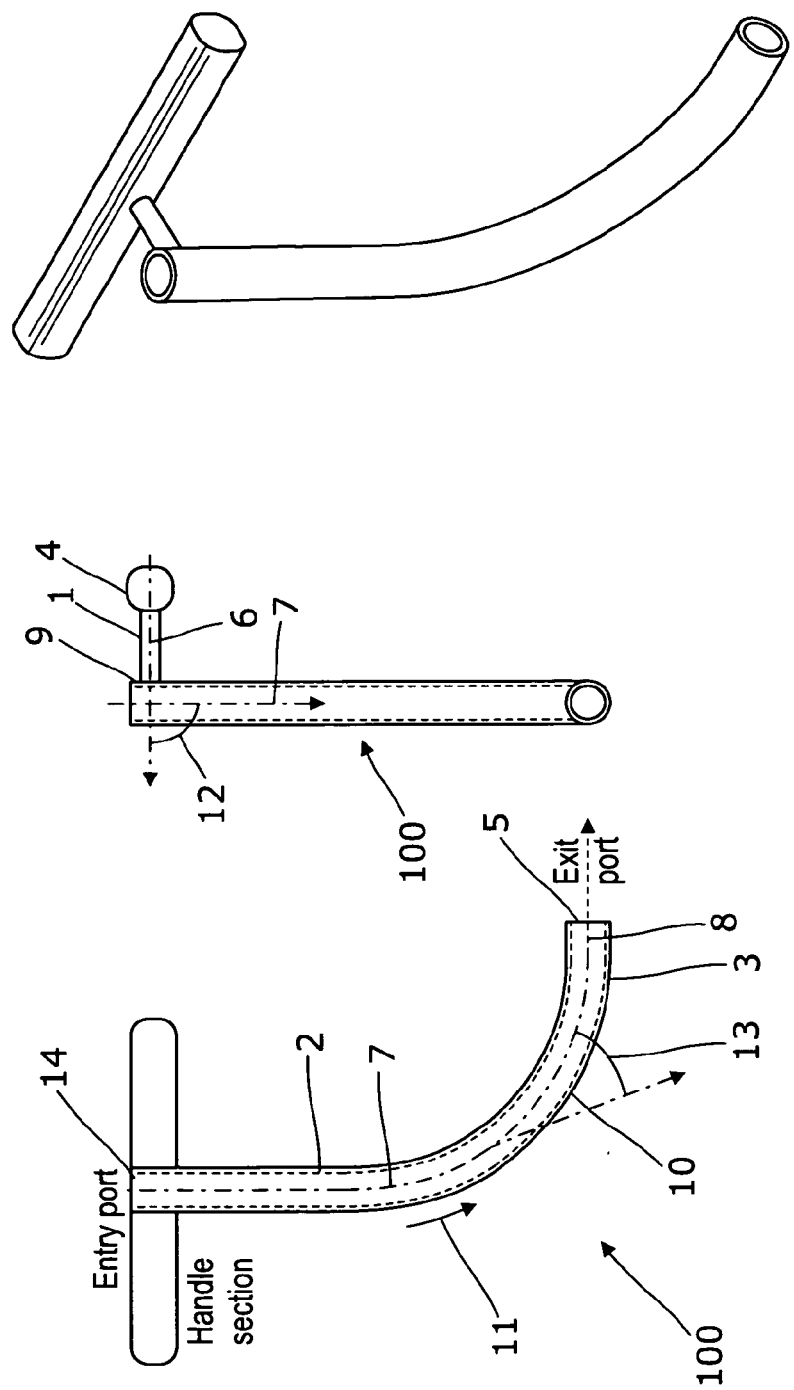

FIG. 5 illustrates an embodiment of the catheter guiding device 100 having a lumen defined by a curved guiding device section 100 between the entry port 14 and the exit port at the distal end 5. The device further comprises a handle section, which may be considered as the proximal section 1, attached to said curved guiding device section. The chest tube enters the lumen of the guiding device 100 through the entry port 14 as illustrated and is diverted through the lumen of the curved guiding device by a medical practitioner and the chest tube exits the guiding device at the distal end 5 thereof in the distal axis 8 direction, which is perpendicular to the direction of the proximal axis 6. In other embodiments, the direction may not be perpendicular.

By observing the relationship between the directions of proximal axis 6 and distal axis 8, as defined by the proximal angle 12 and distal angle 13, relative movement of the distal end with respect to the proximal end may be determined and thus, the medical practitioner will be able to ascertain the direction in which the chest tube is inserted into the pleural cavity.

FIG. 6 illustrates an embodiment of the catheter guiding device 100 having a proximal section 1 and a distal section 3 separated by a mid section 2 comprising an entry port 14 for the insertion of a chest tube. An ergonomically designed handle portion, which may be understood as the proximal section 1, of the device is positioned at the proximal end 4 of the device and defines proximal axis 6 having a proximal direction as represented in the figure. The distal section 3 and the mid section 3, defined by their respective distal axis 8 and mid axis 7, form a distal angle 13 defining a distal bend 10. Similarly, the proximal section 1 and the mid section 3, defined by their respective proximal axis 6 and mid axis 7, form a proximal angle 12 defining a proximal bend 9.

The proximal angle 12 and the distal angle 13 share a relation defining a functional relationship between the movement of the distal end 4 and the proximal end 5. The chest tube enters the lumen of the guiding device through the entry port 14 as illustrated and is diverted through the lumen, defined between the entry port 14 and the exit port at the distal point 5, of the guiding device by a medical practitioner and exits the guiding device at the distal end thereof in a direction of the distal axis. In some embodiments, the direction of exit of the chest tube is at least essentially similar to the proximal axis direction. However, in other embodiments, the direction of exit of the chest tube is not essentially parallel to that of the direction of the proximal axis. In yet another embodiment, the direction of exit of the chest tube is even anti-parallel to the direction of the proximal axis.

By observing the relationship between the directions of proximal axis of the ergonomically designed handle and the distal axis, as defined by the proximal angle and distal angle, relative movement of the distal end with respect to the proximal end may be determined and thus, the medical practitioner will be able to ascertain the direction in which the chest tube is inserted into the pleural cavity.

Figure 7:
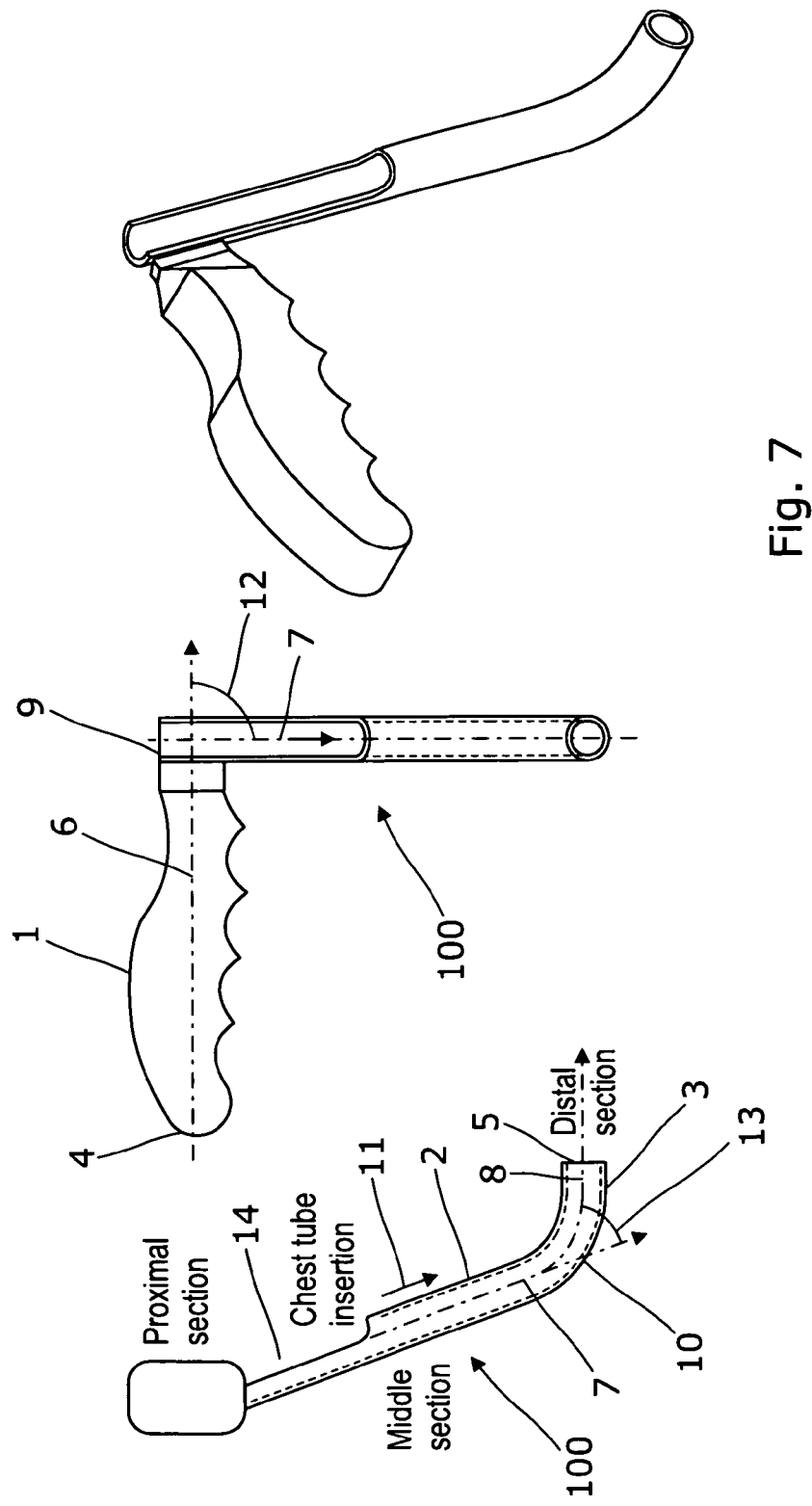

FIG. 7 illustrates the catheter guiding device according to an embodiment of the invention. In principle, the features of this embodiment is same as that of the embodiment illustrated in FIG. 6 except that the chest tube enters the lumen of the guiding device through the entry port 14 as illustrated and is diverted through the lumen, defined between the entry port 14 and the exit port at the distal point 5, of the guiding device by a medical practitioner and the chest tube exits the guiding device at the distal end in a direction perpendicular to direction of the distal axis. In other embodiments, the direction may not be perpendicular.

By observing the relationship between the directions of proximal axis of the ergonomically designed handle and the distal axis, as defined by the proximal angle and distal angle, relative movement of the distal end with respect to the proximal end may be determined and thus, the medical practitioner will be able to ascertain the direction in which the chest tube is inserted into the pleural cavity.

Figure 8:
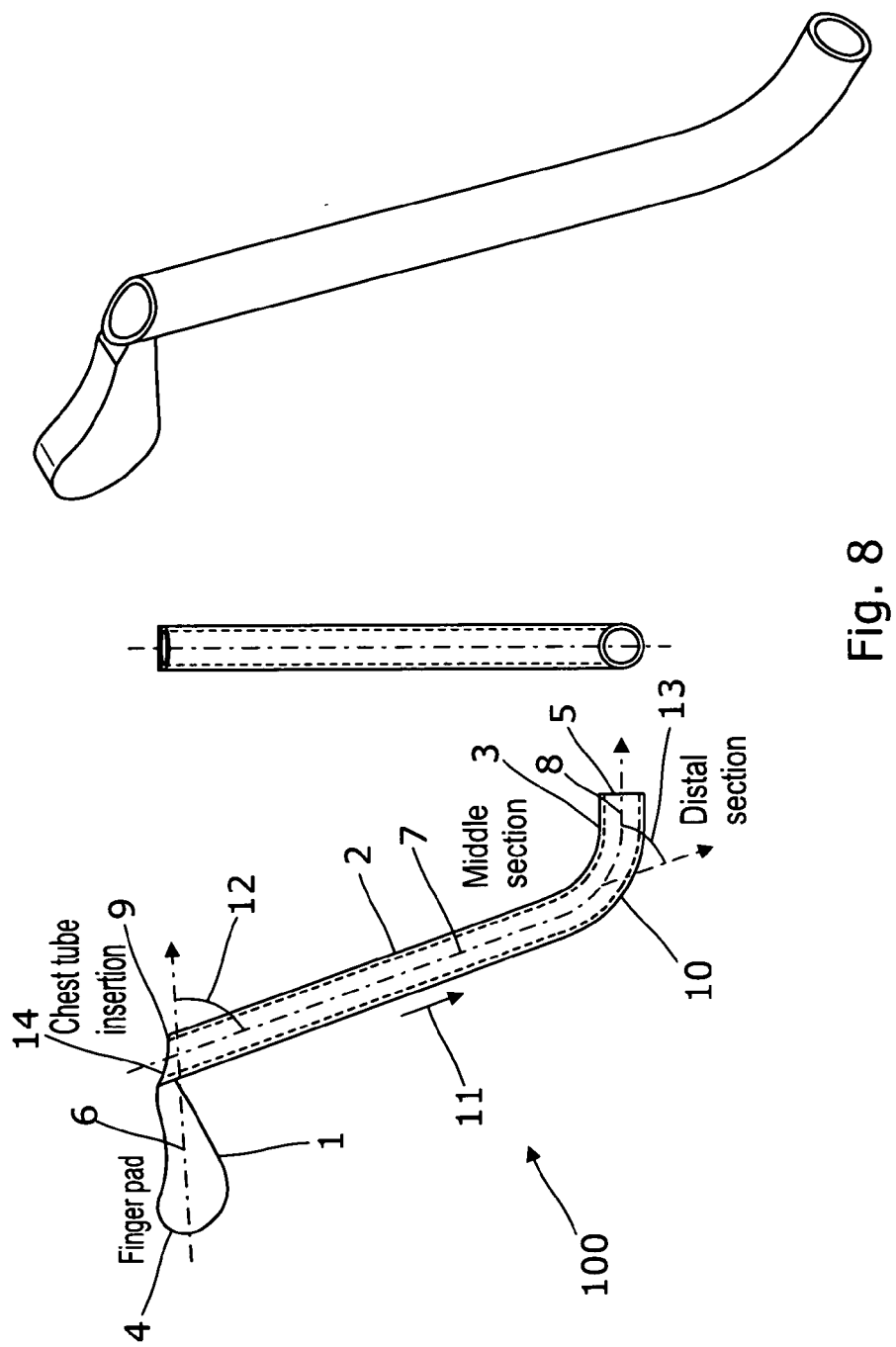

FIG. 8 illustrates an embodiment of the catheter guiding device 100, which is similar to the embodiment disclosed in FIG. 6 except instead of including an ergonomically designed handle portion, a finger pad corresponding to the proximal section 1 in this embodiment is used. The mid section 2 includes an entry port 14 for the insertion of a chest tube as illustrated in the Figure. The chest tube enters the lumen of the guiding device through the entry port 14 as illustrated and is diverted through the lumen of the guiding device 100 by a medical practitioner and the chest tube exits the guiding device at the distal end thereof. The distal section is curved thereby enabling a medical practitioner, e.g. when rotating the device along an axis defined by the middle section of the device, to obtain a correct and accurate direction for exiting the catheter from the guiding device during insertion and accurate location thereof in an intended position of e.g. a pleural cavity.

Figure 9:
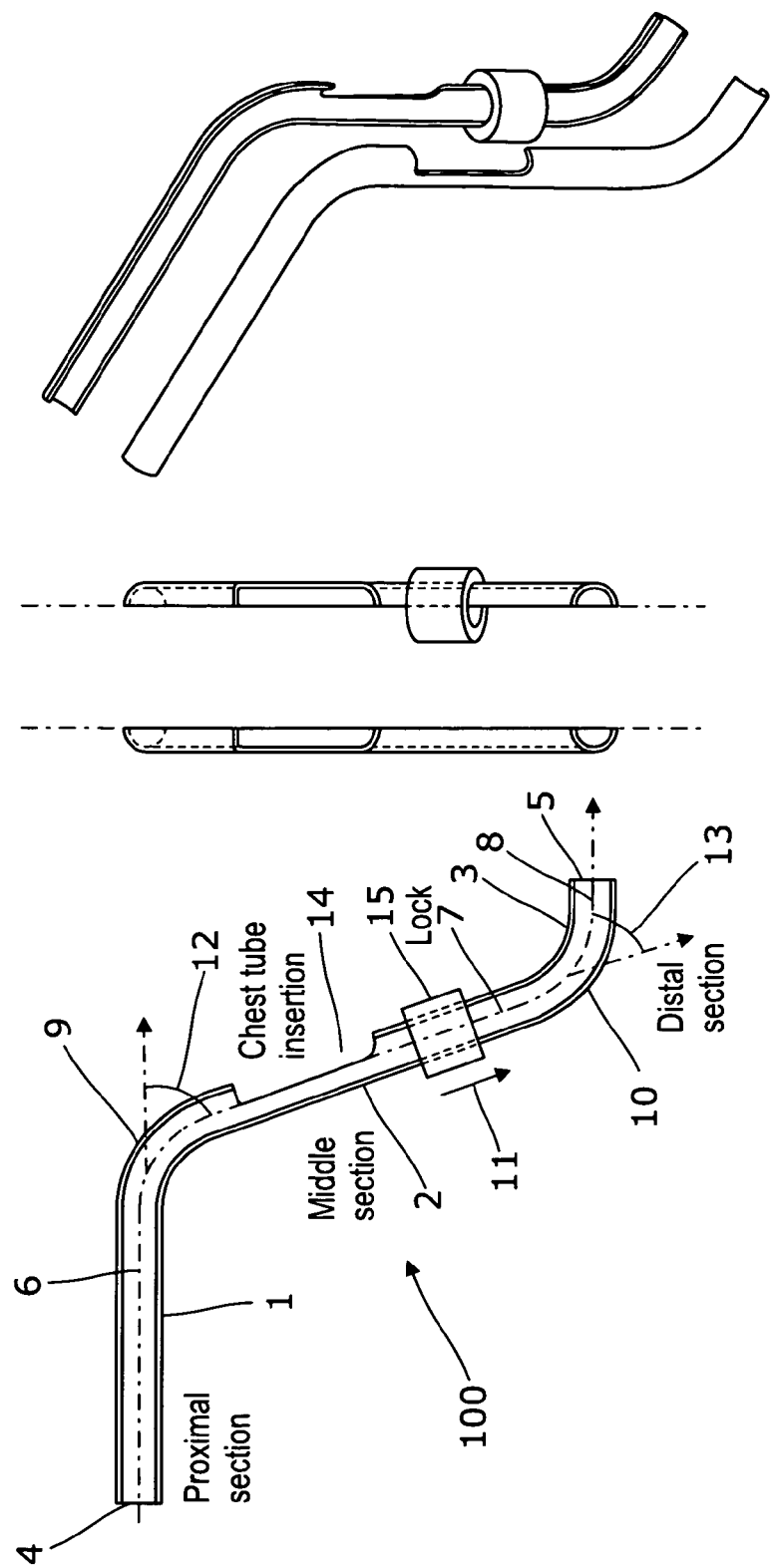

FIG. 9 illustrates an embodiment, wherein the guiding device 100 is in the form of a split-guide in two parts which are held together under practical circumstances by a locking device 15. In the figure, the locking device is in the form of a ring capable of holding the two parts of the guiding device together—thereby de facto forming a structure as illustrated in FIG. 3. The locking device can be a snap-lock which can preferably be operated by one hand only—so that the medical practitioner can hold on to and advance the catheter with the other hand. The entry port 14 for entry of a chest tube is indicated and the bend, distal section comprises a catheter exit port defining a direction for exiting the catheter from the guiding device which in this embodiment is in the same direction, defined by distal axis 7, as the straight, direction of proximal axis 6 of the proximal section 1 which serves the purpose of a handle for the medical practitioner to hold on to. By observing the direction of the handle, defined by the proximal axis 6, the medical practitioner will be able to ascertain the direction in which the chest tube is being advanced in the body cavity of an individual.

The device is in a two-part form comprising a proximal end, a distal end, a lumen capable of receiving a catheter, and a locking means; wherein, the lumen comprises at least one catheter entry port and at least one catheter exit port located at the distal end; and the proximal end, lumen and the distal end are separable in two parts along the axial length of the guiding device.

FIG. 10 is a representative illustration of the positioning of the catheters performed in accordance with the experiment conducted and disclosed in the example of the present application. The arrows indicate the tip of the catheter.

FIG. 11 illustrates different cross-sectional embodiments 200 of a catheter according to the present invention. FIG. 11A illustrates a catheter having reinforced side walls 205 preventing or reducing any undesirable sidewards (i.e. lateral) movement when the catheter is inserted. The dimensions of the guiding device are adapted to the respective geometrical cross-sectional configuration of the catheter, in this embodiment of the invention, such that the lumen of the catheter guiding device can receive the catheter even when the catheter has essentially a non-circular cross-section (cf. FIG. 11A). FIG. 11B illustrates a catheter 200' having an essentially circular cross-section.

FIG. 12 illustrates a catheter guiding device 100 having a distal section 3 and a mid section 2. This embodiment is essentially similar to the device disclosed in FIG. 5. However, in this embodiment, the device does not separately include a proximal section. In this embodiment, the mid section includes the proximal end 4. Person skilled in the art would appreciate that in such situations, a small part of the mid section 2 including and near the proximal end 4 may be considered as a proximal section and the mid axis may be representative of proximal axis, for understanding purposes and therefore, complies with the requirement that the proximal end is closer and accessible to the medical practitioner when the guiding device 100 is in use.

By observing the relationship between the movement of the proximal axis, which may be considered to be represented by mid axis 7, and the distal axis 8 forming the distal angle, relative movement of the distal end with respect to the proximal end may be determined and thus, the medical practitioner will be able to ascertain the direction in which the chest tube is inserted into the pleural cavity.

Figure 13:
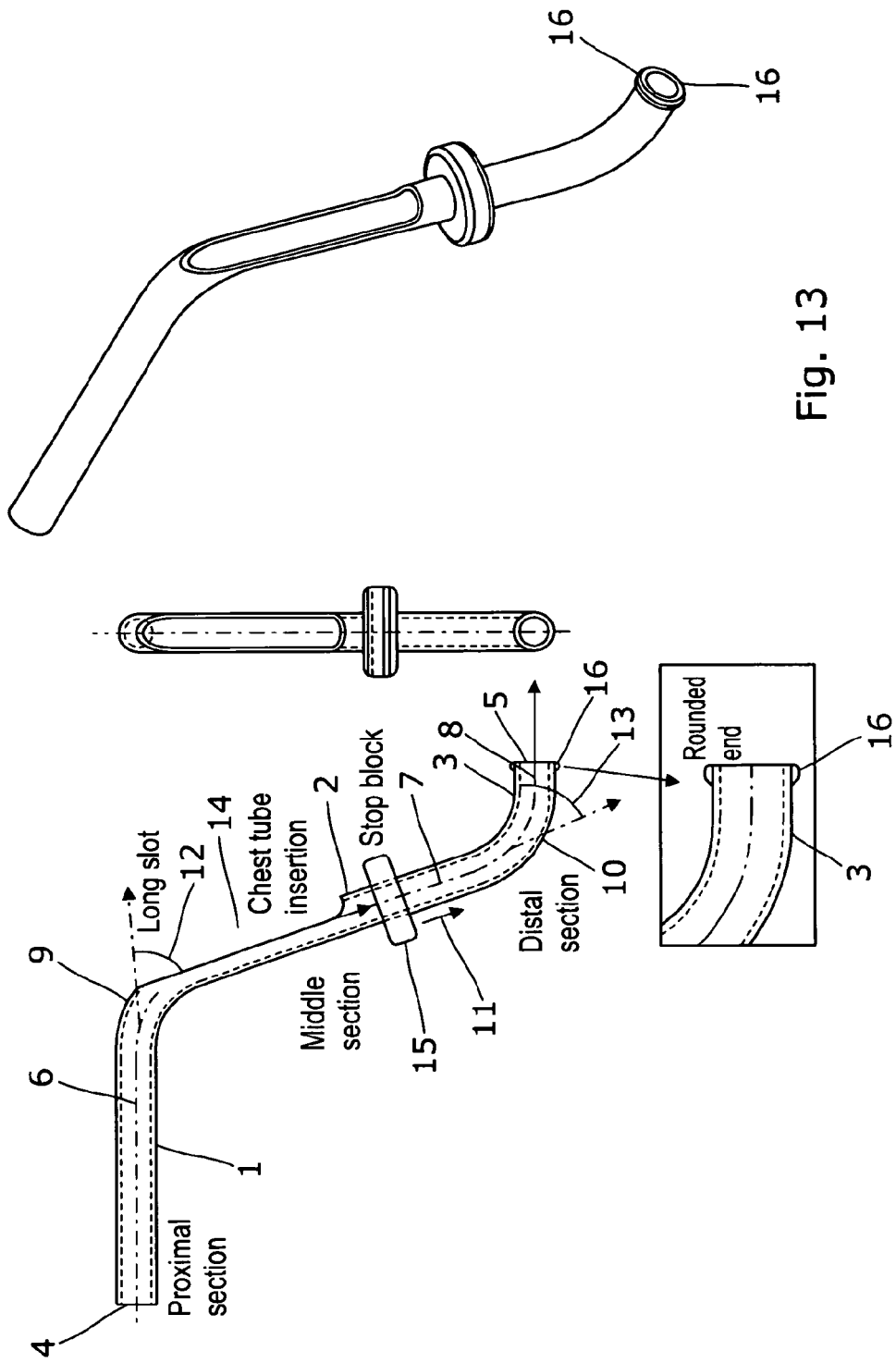

FIG. 13 illustrates the catheter guiding device 100 according to an embodiment of the invention. As an additional feature, the guiding device includes rounded end 16 of the distal end 5. In comparison to a guiding device having relatively sharper or abrupt edges at the distal end, the rounded end 16 potentially minimizes the risk of injury to organs when the guiding device is inserted in the body cavity.

Figure 14:
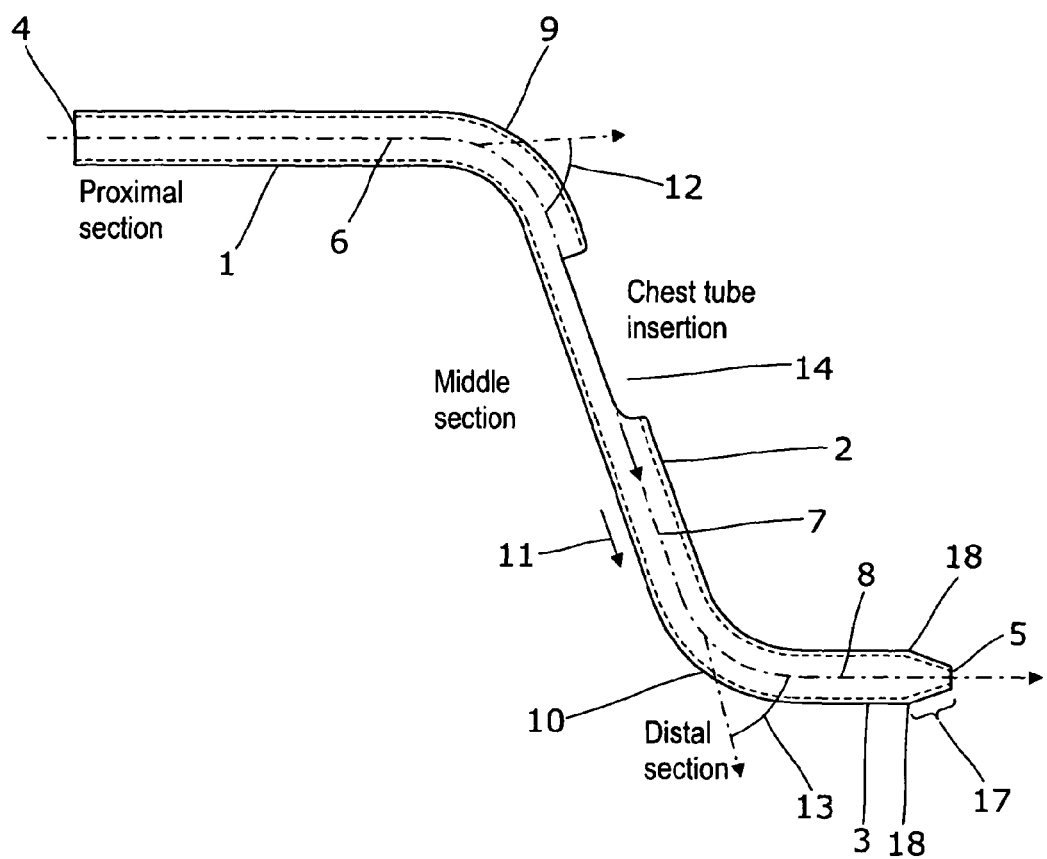

FIG. 14 illustrates the catheter guiding device 100 according to an embodiment of the invention. As an additional feature, the guiding device includes a part of the distal section 17, which is tapered inwards along the direction of the distal axis, from an edge close to the distal end 5 until the distal end 5. This improves access abilities of the distal section in the body cavity and easier insertion of the guiding device because the tapered end moves with lesser resistance in the body cavity as opposed to non-tapered ends. In one embodiment, the edge 18 where the tapering in the distal section starts may also be made as a rounded edge in order to reduce injury because of abrupt or sharp edge 18. In another embodiment, the tapering may be extremely gradual over a relatively large distance of distal section 3, staring from 18 until the distal end 5. Such relatively large distance may be ascertained by the skilled person based on the circumstances, such as type of body cavity, condition of the patient, etc.

Person skilled in the art would appreciate, that the features of FIG. 13 and FIG. 14 may be incorporated in the same guiding device.

Figure 15:
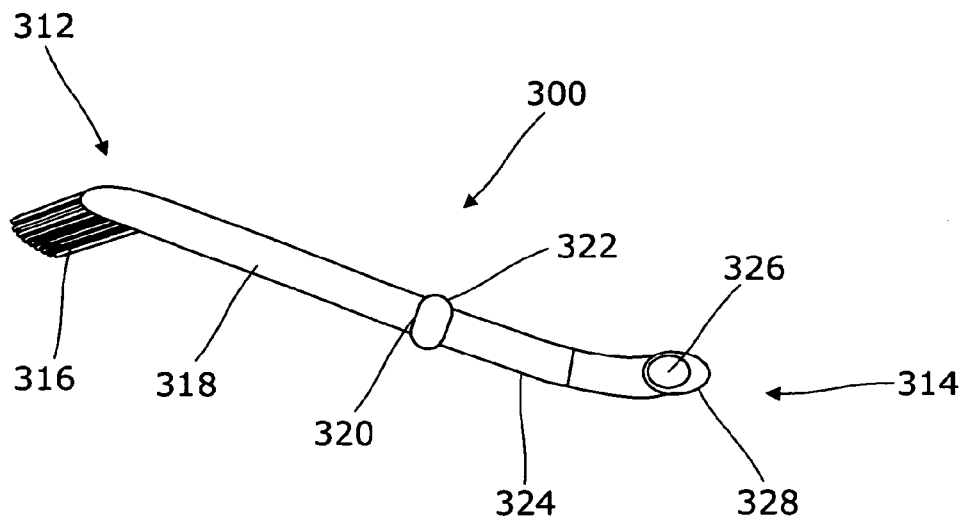

FIG. 15 is a perspective view of another embodiment of the guiding device of the invention comprising a tip at the distal end portion.

Figure 16:
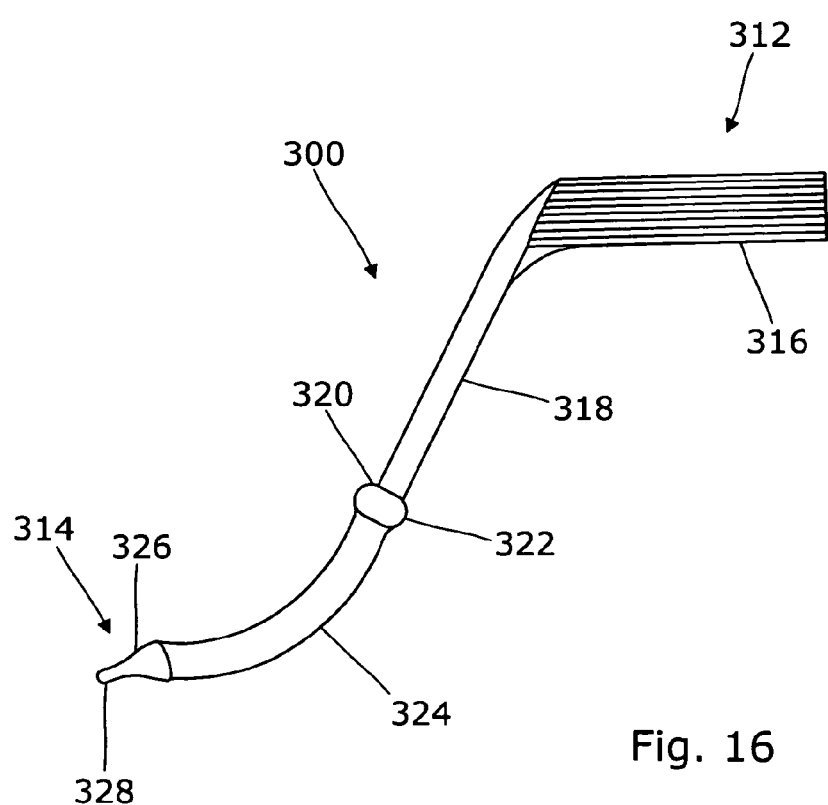

FIG. 16 is a side view of the embodiment shown in FIG. 15.

Figure 17:
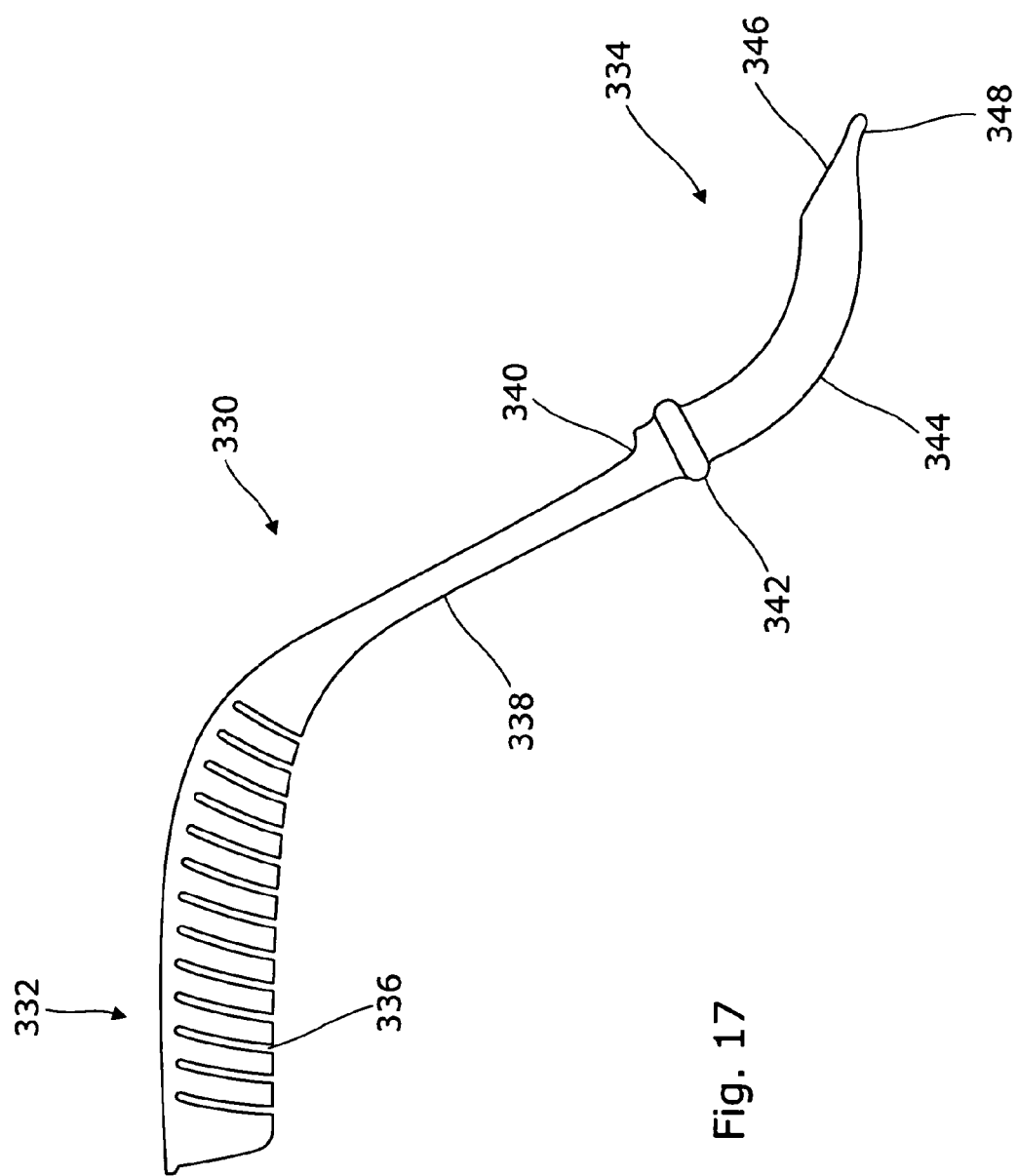

FIG. 17 is a side view of another embodiment of the guiding device of the invention a tip at the distal end portion.

Figure 18:
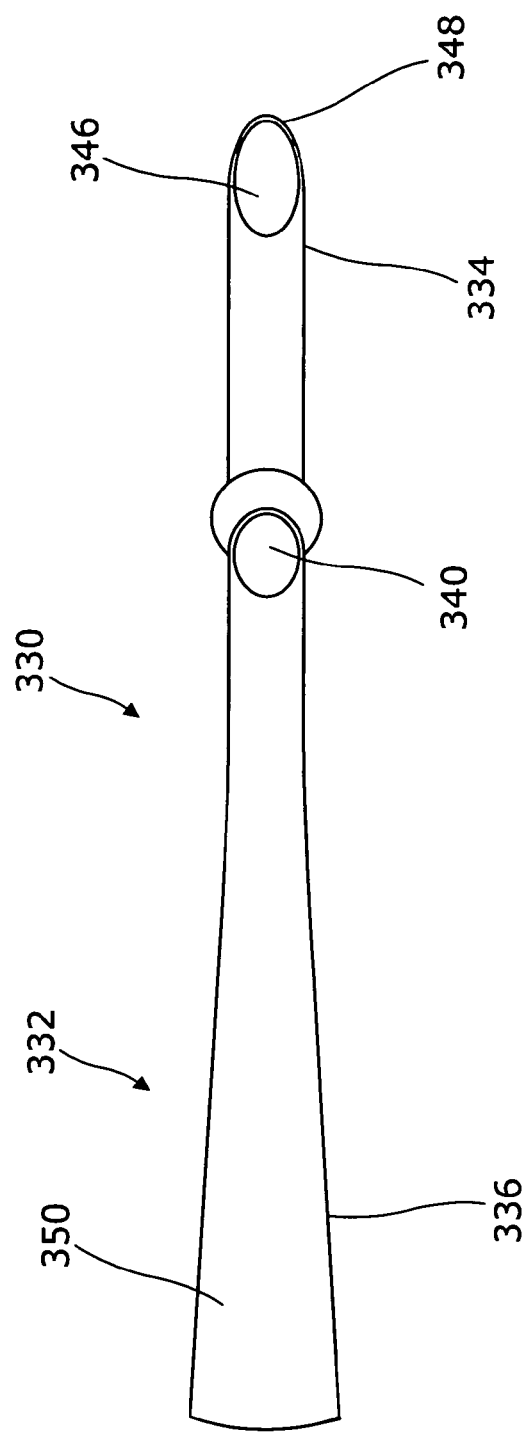

FIG. 18 is a plan view of the embodiment shown in FIG. 17.

Figure 19:
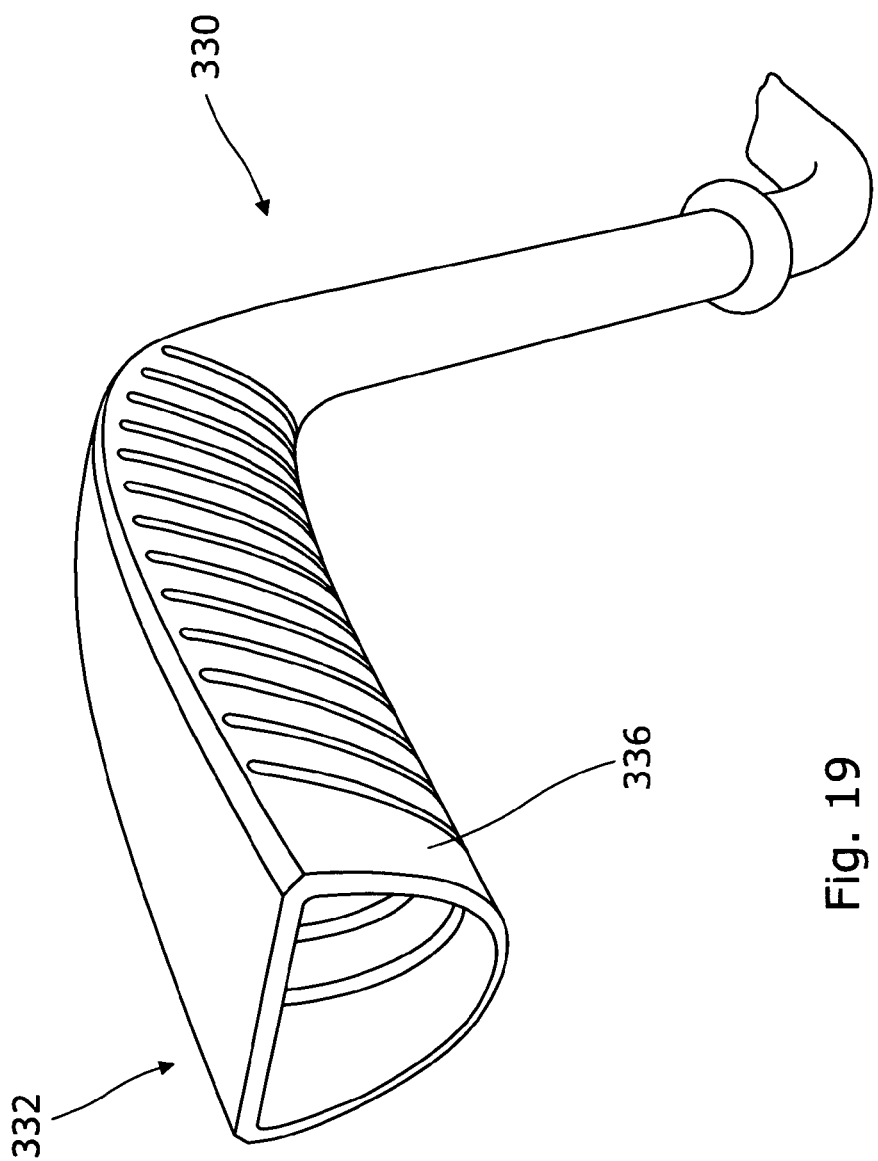

FIG. 19 is a perspective view of the embodiment shown in FIG. 17 showing details of the proximal end of the device.

Figure 20:
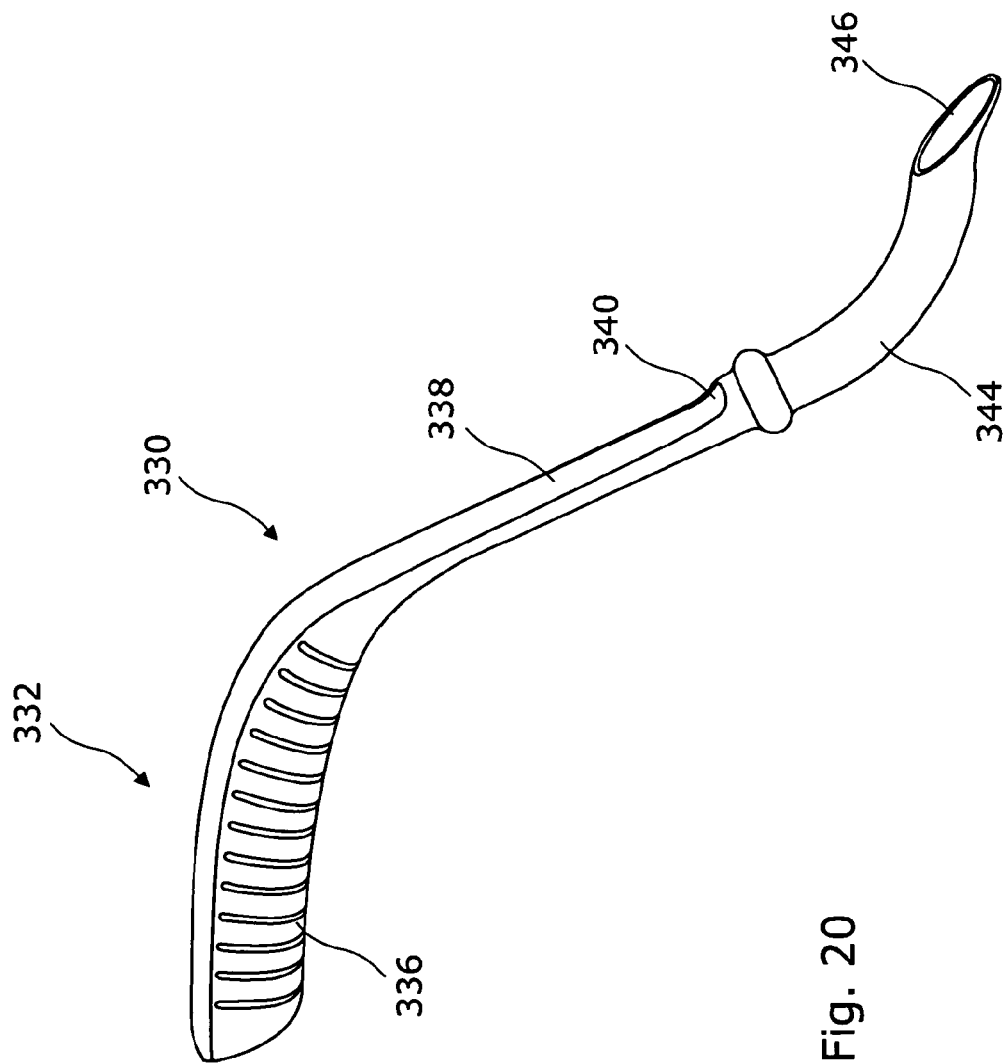

FIG. 20 is a perspective view of the embodiment shown in FIG. 17 showing details of the distal end of the device.

FIG. 21 is a cross-sectional view of an embodiment of the guiding device of the invention provided with a removable bung in the lumen at the distal end of the device.

FIG. 22 is a front view of the embodiment shown in FIG. 21.

FIG. 23 is a perspective view of the embodiment shown in FIG. 21.

Figure 24:
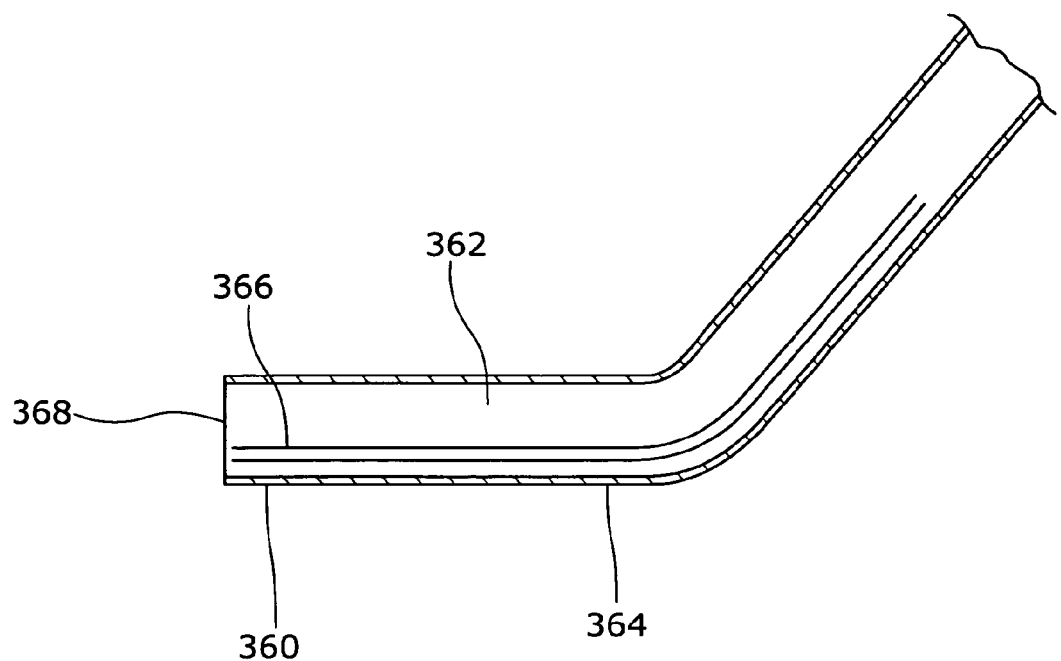

FIG. 24 is a partial cross-sectional view of an embodiment of the guiding device of the invention showing projections in the lumen.

Figure 25:
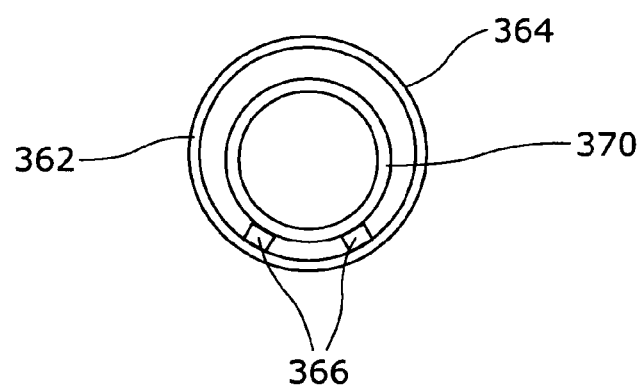

FIG. 25 is an end-on view of the embodiment shown in FIG. 24 showing a catheter within the lumen.

DETAILED DESCRIPTION OF THE INVENTION

According to an embodiment of the invention, a catheter guiding device is disclosed. The catheter comprises a proximal end, a distal end, at least a distal bend or a curved section, and a lumen capable of receiving a catheter. The lumen comprises at least one catheter entry port and at least one catheter exit port located at the distal end. The at least one catheter entry port and said at least one catheter exit port are separated by the at least a distal bend or a curved section.

The catheter device is capable of directing the insertion of the catheter into a body cavity when the catheter exits the catheter exit port, thereby ensuring an accurate positioning of the catheter into the body cavity of an individual at an intended, predetermined position thereof.

The catheter may comprise of a chest tube and the body cavity is a pleural cavity of an animal or human body. The catheter exit port is separated from the catheter entry port by at least one section of the catheter guiding device having a bend or curved section.

In one embodiment, the curved section is essentially a circular arc. In another embodiment, the bend forms a distal angle, measuring more than 0 degrees but less than 180 degrees.

In an embodiment, the device includes a functional relationship between the movement of the proximal end and the distal end. The functional relationship may be determined by the measure of distal angle and/or the length of a distal section. A person skilled in the art would appreciate that prior knowledge of the measure of the distal angle, and the length of the distal section would allow the medical practitioner to operate or move the distal end of the device in a controlled and reliable manner, in order to position the distal end at the intended location in the body cavity. Therefore, the direction of movement and positioning of the catheter in the body cavity can be accurately achieved. The length of the distal section may be a few centimeters and is easily ascertainable by the skilled person based on the circumstances, such as type of body cavity, condition of the patient, etc.

In an embodiment of the invention, the functional relationship determines position of the distal end in the body and defines the direction in which the catheter exits the catheter exit port, the direction being along a distal axis.

In yet another embodiment of the invention, the guiding device also includes a proximal section including the proximal end; a mid section including the lumen and the catheter entry port; and a distal section including the distal end and the catheter exit port. The proximal section forms a proximal angle with the mid section; and the distal section forms the distal angle with the mid section, the distal angle defining the distal bend.

In an embodiment, the device includes a functional relationship between the movement of the proximal end and the distal end. The functional relationship includes measure of the proximal angle and measure of the distal angle and/or the length of the distal section, which may be a few centimeters and is easily ascertainable by the skilled person based on the circumstances, such as type of body cavity, condition of the patient, etc.

The functional relationship determines position of the distal end in the body; and defines the direction in which the catheter exits the catheter exit port, the direction being along a distal axis. A person skilled in the art would appreciate that prior knowledge of the measure of the distal angle, proximal angle and the length of the distal section would allow the medical practitioner to operate or move the distal end of the device in a controlled and reliable manner, in order to position the distal end at the intended location in the body cavity. Therefore, the direction of movement and positioning of the catheter in the body cavity can be accurately achieved.

In an embodiment, the measure of the proximal angle and distal angle are more than 0 degrees but less than 180 degrees.

In another embodiment, the proximal angle and the distal angle are selected from a group comprising acute angles, obtuse angles, right angles, and a combination thereof. In yet another embodiment, the proximal angle and the distal angle are selected from a group comprising a pair of supplementary angles, a pair of complementary angles, and a pair of right angles.

In another embodiment of the invention, a two-part guiding device is disclosed. The two-part guiding device includes a proximal end, a distal end, a lumen capable of receiving a catheter; wherein the lumen comprises at least one catheter entry port and at least one catheter exit port located at the distal end; and the proximal end, lumen and the distal end are separable in two parts along the axial length of the guiding device. The length of the distal section may be a few centimeters and is easily ascertainable by the skilled person based on the circumstances, such as type of body cavity, condition of the patient, etc.

The guiding device may include any of the features of the single piece guiding device, as disclosed with reference to FIGS. 3-8 and 12.

In an embodiment, the two-piece guiding device further includes a locking means, such as a snap lock, for holding together the two-part of the guiding device together and the axial length is selected from a group of length of proximal axis, length of mid axis, length of distal axis and a combination thereof.

In one embodiment, the present invention relates to a simple, safe and accurate method of inserting and placing a chest tube into the pleural cavity, by using the blunt dissection technique.

Drainage of a pleural effusion (thoracentesis) is a common procedure in thoracic surgery. The procedure involves insertion of a chest tube into the pleural cavity of an individual. The chest tube is used e.g. to remove air (collapsed lung), fluids (pleural effusion, blood, chyle) or pus (empyema) from the pleural cavity. The method for performing thoracentesis according to the present invention facilitates that the chest tube is accurately positioned in the pleural cavity at an intended position therein. The problem of not always being able to direct a catheter or chest tube to a particular location in the pleural cavity is recognised in the art, cf. herein above.

Drainage of a pleural effusion is primarily done to relieve the symptoms of the effusion. The symptoms of a pleural effusion commonly include shortness of breath, chest pain, or dry cough. Drainage of a pleural effusion may also alleviate or terminate an inflammation cycle e.g. associated with a pneumonia-associated (parapneumonic) effusion. The fluid drained from a pleural effusion is in one embodiment of the present invention sent off for analysis and/or diagnosis and the fluid may thus provide valuable clues as to the likely cause of the effusion and the symptoms associated therewith.

Accordingly, drainage of a pleural effusion according to the present invention can be used in combination with a diagnostic test to evaluate a likely cause of the pleural effusion. Accordingly, in one embodiment, a cytopathological evaluation ex vivo of collected pleural fluid may be required in order to determine the causes of the abnormal accumulation of pleural fluid. A cytopathological evaluation ex vivo can be carried out in combination with one or more diagnostic tests selected from e.g. clinical microscopy, microbiology, chemical analysis, tumor marker evaluation and pH determination. Accordingly, in one embodiment, the cause of e.g. an infection and/or a malignancy within the pleural cavity can be identified using the above-cited, diagnostic methods according to the present invention.

In spite of the existence of a vast number of available diagnostic tests, many pleural effusions remain idiopathic in origin and if severe symptoms arise and/or persist, invasive techniques may be needed and treatment may be required to relieve the observed pleural effusion symptoms.

Pneumothorax is another clinical condition subject to treatment or amelioration in accordance with the methods of the present invention. Under normal physiological conditions, the pressure within the pleural cavity is below atmospheric pressure. When this pressure changes because of excess air and/or fluid entry into the pleural cavity, the lung may collapse. Pneumothorax (collapsed lung) can in principle occur as a result of a disease or an accident. For example, the chest wall may inadvertently be punctured during surgery or e.g. as result of an accident or violence. Also, the lung itself may be accidentally punctured or cut. In both cases, drainage of the pleural cavity will most likely be required. In case of pneumothorax, a catheter in the form of a chest tube can be diverted into the pleural cavity by the methods of the present invention to restore the intrapleural pressure and to reinflate a punctured and collapsed lung.

As will be clear from the above, the catheter guiding device according to the present can be used for inserting and accurately positioning chest tubes used in surgical procedures for draining pleural effusions or for treating or ameliorating pneumothorax.

The catheter guiding device according to the present invention defines a lumen into which a catheter can be inserted through a first opening, or entry port, of the catheter guiding device. In one embodiment, a second opening, or catheter exit port, of the catheter guiding device is separated from the first opening of the device by at least one section of the device defining a curved form through the lumen of which the catheter can be diverted after having entered the first opening (entry port) and before exiting the second opening (exit port) of the catheter guiding device. A curved section of the catheter guiding device is preferably located at the distal end thereof, i.e. the end of the guiding device which is inserted into a body cavity during use.

In one embodiment, at least one catheter guiding device section is essentially straight and e.g. forms a handle suitable for the medical practitioner to hold on to when operating the catheter guiding device during use thereof in a surgical procedure—e.g. when inserting a pleural catheter in a pleural cavity. The handle can be ergonomically formed to generate a grip for either a right handed practitioner or a left handed practitioner, or the handle can be formed in such a way that it fits equally well both a right handed as well as a left handed medical practitioner operating the guiding device.

The catheter guiding device can comprise one or more, such as typically one, two or three physically connected and at least essentially curved or circular arc formed section(s) in the absence of any straight guide section(s)—such as guide sections e.g. forming a handle.

In another embodiment, the catheter guiding device comprises both one or more at least essentially curved section(s), such as one, two or three physically connected and at least essentially curved or circular arc formed section(s), and one or more, such as one, two or three essentially straight, i.e. non-curved section(s), such as for example a straight section capable of serving as a handle section for a medical practitioner to hold on to when operating the catheter guiding device under practical circumstances.

The at least one section of the guide defining a curve defines a distal angle between 0 degrees to 180 degrees. The angle will depend on the design of the guiding device as disclosed in more detail herein below.

In one embodiment, the angle between i) the axial direction of the catheter when the catheter enters the first catheter guiding device (entry port) opening, that is mid axis, and ii) the axial direction of the catheter (located in e.g. a pleural cavity) when the catheter exits the catheter guiding device from the second (exit port) opening, that is distal axis thereof is preferably in the range of from 90 degrees to preferably less than 180 degrees, such as in the range of from 90 degrees to preferably less than 150 degrees, for example in the range of from 90 degrees to preferably less than 140 degrees, such as in the range of from 90 degrees to preferably less than 130 degrees, for example in the range of from 90 degrees to preferably less than 120 degrees, such as in the range of from 100 degrees to preferably less than 150 degrees, for example in the range of from 100 degrees to preferably less than 140 degrees, such as in the range of from 100 degrees to preferably less than 130 degrees, for example in the range of from 100 degrees to preferably less than 120 degrees, such as in the range of from 110 degrees to preferably less than 150 degrees, for example in the range of from 110 degrees to preferably less than 140 degrees, such as in the range of from 110 degrees to preferably less than 130 degrees, for example in the range of from 110 degrees to preferably less than 120 degrees.

The curved section can have various forms as long as the curved section of the guiding device, when the device is being operated by a medical practitioner under practical circumstances, defines an axial direction, i.e. distal axis, of the exit port of the guiding device in a correct and intended orientation in a body cavity, such as e.g. a pleural cavity, i.e. an orientation that can aid the medical practitioner in accurately directing e.g. a chest tube located in the lumen of the guiding device to an intended position of e.g. a pleural cavity. The curved section can for example be an at least essentially circular arc, or an at least essentially parabolic curve, or an at least essentially hyperbolic curve, or an at least essentially elliptic curve.

A medical practitioner can divert the catheter guiding device comprising e.g. a curved section located in the distal end thereof, such as an at least essentially circular arc formed section, through an incision defining an access port to e.g. a pleural cavity, thereby locating the distal end of the catheter guiding device in said pleural cavity. By moving the outer part of the catheter guiding device (i.e. the part of the guiding device not inserted in the pleural cavity through the incision defining an access to the pleural cavity) side ways, or up or down, while also retaining the option of being able to rotate the guiding device along the axis defined by the incision, the medical practitioner has essentially full freedom to adjust and decide the axial direction in which the catheter is to exit the exit port of the device and enter the pleural cavity, during insertion therein, prior to being accurately positioned at an intended position of the pleural cavity defined by direction and distance relative to the point of entry of the pleural cavity.

Based on the above disclosure, it will be understood that the exact design of the curved section(s) of the device is/are not critical as long as a catheter located in the lumen of the catheter guiding device can be directed accurately to an intended position of a body cavity by operating the guiding device in such a way that the exit port of the device defines the direction in which the catheter is to be inserted into the body cavity.

In one embodiment, the axial orientation of an essentially straight handle section of the guiding device defines the orientation in which the catheter located in the lumen of the guiding device exits the exit port of the guiding device in the pleural cavity.

According to this embodiment, the device may comprise at least two curved sections, i.e. proximal bend and distal bend, wherein the two curved sections are operably linked by a connecting section, i.e. mid section, which can be an essentially straight connecting section, or itself adopt the form of e.g. a curve, such as illustrated e.g. in FIG. 3 and thus define the distal section.

By observing the axial direction, proximal axis direction, defined by the straight handle section in this embodiment, a medical practitioner will be able to determine the direction, i.e. distal axis direction, of the catheter as it exits the exit port of the guiding device in the pleural cavity, as this direction is the same as the axial direction, i.e. proximal axis direction, defined by the straight handle section.

Various polymer materials approved for surgical procedures can be used for the manufacture of the guiding device, including moldable polymers of medical grade. When the guiding device is intended for multiple use the polymer composition must be sterilizable. The guiding device can also be manufactured from optionally coated titanium.

The cross-section of the lumen of the guiding device is preferably at least essentially circular—so as to fit the insertion of a catheter also having a circular cross-section. However, other geometrical cross-sections can also be envisioned. As illustrated in FIG. 11, panel A, one can imagine using a catheter tubing having reinforced side-walls so as to prevent undesirable lateral movement of the catheter during insertion thereof into a body cavity.

The cross-section of the lumen can be essentially circular when the distance from the centre of the cross-section to any point on the periphery of the cross-section is in the range of from a quarter of the average distance from the centre of the cross-section to any point on the periphery of the cross-section to preferably less than four times the average distance from the centre of the cross-section to any point on the periphery of the cross-section. The cross-section of the lumen of the guiding device and the cross-section of the catheter to be inserted therein should be compatible.

FIGS. 15 and 18 show a guiding device 310 having a proximal portion 312 and a distal portion 314. The device 310 is constructed from polypropylene, although other biocompatible materials, preferably polymeric materials, could be used. The proximal portion 312 contains a handle portion 316 in the form of a ribbed cylindrical section, for ease of gripping by the user. The handle portion leads to a central substantially straight and concave portion 318 of the device, which itself leads to an opening 320 towards the distal end of the device. The opening 320 defines an entry port for the insertion of a catheter. The outer wall of the device forms a curved annular portion 324 leading from the entry port 320 to the distal end of the device, forming a lumen for guiding a catheter through the device. The annular portion leads to an opening 326 defining the exit port for the catheter.

The outer wall of the device defines a projecting collar or rim 322 distal of the entry port 320 to provide the user with a defined stopping point to aid the correct insertion of the guiding device 310 into a patient's body. The device 310 is inserted into the patient's body until the rim 322 comes near to or contacts the patient's ribs.

The distal end 314 of the device 310 is also provided with a projecting tip 328. In the embodiment shown, the tip is in the form of a lip 328 projecting beyond the exit port 326. The lip 328 aids the insertion of the device into a patient's body, particularly when the device is being inserted patient's ribs towards their pleural cavity.

FIGS. 17, 18, 19 and 20 show another embodiment of the guiding device 330 of the invention having a proximal portion 332 and a distal portion 334. The device 330 is constructed from polypropylene, although other biocompatible materials, preferably polymeric materials, could be used. The proximal portion 332 contains a handle portion 336 in the form of a hollow ribbed cylindrical section, for ease of gripping by the user. The handle portion is provided with a number of gaps in the outer wall defining the device in order to improve grip. The handle portion leads to a central substantially straight and concave portion 338 of the device, which itself leads to an opening 340 towards the distal end of the device. The opening 340 defines an entry port for the insertion of a catheter. The outer wall of the device forms a curved annular portion 344 leading from the entry port 340 to the distal end of the device, forming a lumen for guiding a catheter through the device. The annular portion leads to an opening 346 defining the exit port for the catheter.

The outer wall of the device defines a projecting rim 342 distal of the entry port 340 to provide the user with a defined stopping point to aid the correct insertion of the guiding device 330 into a patient's body. The device 330 is inserted into the patient's body until the rim 342 comes near to or contacts the patient's ribs.

The distal end 334 of the device 340 is also provided with a projecting tip 348. In the embodiment shown, the tip is in the form of a lip 348 projecting beyond the exit port 346. The lip 348 aids the insertion of the device into a patient's body, particularly when the device is being inserted patient's ribs towards their pleural cavity.

FIG. 18 shows that the handle portion 336 is provided with indicia 350, which helps to distinguish the proximal end 332 from the distal end 334, especially for users unfamiliar with the device. The proximal and distal ends could also or alternatively be distinguished from one another by the use of colours or shapes, for example by having noticeably different cross-sections.

FIG. 18 also clearly shows the entry port 340 and exit port 346, defining the route through which a catheter would be guided through the device and into the correct anatomical location within the patient.

FIG. 19 more clearly shows that the handle portion 336 of the proximal end 332 is hollow, with a semi-circular cross-section. The handle portion contains numerous gaps or ribs in the outer wall of the device in order to help the use grip the device securely when in use.

FIG. 20 shows the concave central portion 338 of the device 330 which leads into the entry port 340. The concave shape of the central portion 338 helps a user to feed a catheter into the entry port 340, to be guided by the curved section 344 to exit the device via the exit port 346.

FIGS. 21, 22 and 23 show a preferred feature which can be applied to all of the guiding devices of the invention. The device 340 comprises a proximal end 342 leading to a distal end 344. The outer wall of the device 40 devices a catheter entry port 346 leading to a lumen 350, and then leading to a catheter exit port 348. The device 340 also contains a removable plug 352 in the exit port 348 at the distal end 344 of the device. Attached to the plug 352 is a thread 354 which passes back through the lumen 350 to exit the entry port 346. The plug 352 has a rounded end projecting out of the catheter exit port 348, although other shapes could be used.

The projecting plug 352 helps with the insertion of the device 340 into the patient's body. The rounded end of the plug 352 helps to facilitate the passage of the distal end of the device through the tissue of the patient into the desired correct anatomical location. Once the device is in place, the user can pull on the thread 354 to draw the plug 352 back through the lumen and out of the entry port 346. The plug 352 is made from polypropylene, although other materials could be used in other embodiments.

FIG. 24 is a cross-sectional view of the distal end 360 of another embodiment, comprising a lumen 362 defined by an annular outer wall 364. The lumen is provided with projections 366 to facilitate the passage of a catheter between the entry port and the exit port 368.

FIG. 25 is a view looking into the exit port 368 of the device shown in FIG. 24. The projections 366 comprise a pair of raised lines or rails on the inner surface of the lumen. The rails 366 lift the catheter 370 away from the lumen wall to prevent sticking forces such as friction. The catheter can thus be passed through the device in an easy manner to facilitate its insertion in the patient's body. Although the device is shown having projections in the form of a pair of rails, other embodiments could have one, two or more projections, and the projections need not be in the form of a raised line. Alternatively, or in addition, the lumen may be provided with a lubricious material to facilitate the passage of the catheter.

Methods for Insertion of a Chest Tube in the Pleural Cavity

The following, detailed disclosure of various procedures for the insertion of chest tubes into the pleural cavity is intended to provide a general introduction to such procedures. Deviations from the disclosed procedures can occur and such deviations will be well known to the skilled artisan. The skilled artisan will be aware of general, state-of-the-art surgical procedures for the insertion of chest tubes into the pleural cavity. Surgical steps for the insertion of e.g. chest tubes into the pleural cavity of an animal or human body are well known in the art.

The point of insertion of a catheter in the pleural cavity can occur on the side (lateral thorax), generally at a line drawn from the armpit (anterior axillary line) to the side (lateral) of the nipple in males, or to the side (about 2 inches [about 5 cm]) above the sternoxiphoid junction (lower junction of the sternum, or chest bone) in females.

The British Thoracic Society recommends that a chest tube is inserted in an area described as the "safe zone", which is a region bordered by: the lateral border of pectoralis major, a horizontal line inferior to the axilla, the anterior border of latissimus dorsi and a horizontal line superior to the nipple. More specifically, the tube is inserted into the 5th intercostal space slightly anterior to the mid axillary line. Klopp et al. (2009) (ibid.) states that the most appropriate site for the insertion of a chest tube into the pleural cavity is the 4th or 5th intercostal space in the mid- or anterior-axillary line.

The skin is routinely sterilized with antiseptic solution covering the relevant area, and local anesthesia can be administered to minimize discomfort. At the rib chosen for insertion, the skin over the rib is anesthetized e.g. with lidocaine (or any other suitable, local anesthetic agent as the case may be) using e.g. a 10-cc syringe and e.g. a 25-gauge needle. At the rib below the rib chosen for pleural insertion, the tissues, muscles, bone, and lining covering the lung are also anesthetized using e.g. a 25-gauge needle.

Medical practitioners will be expected to take precautions to keep the surgical procedure sterile, including the usage of sterile gown, facemask, and eye protection. All equipment must be sterile as well and universal precautions are followed for blood and body fluids.

The correct chest tube size can be selected depending on the clinical indication observed and the patient to be treated. An 18-20 F(rench) catheter is typically used for pneumothorax, a 32-36 F catheter is typically used for hemothorax, whereas trauma patients often require a 38-40 F catheter size. Children, especially infants, will generally require smaller tube sizes than those stated herein above.

Before drainage of a pleural effusion is performed, a chest x-ray or CT-scan may be ordered to confirm the presence of e.g. a pleural effusion and to establish the precise location in the pleural cavity of the pleural effusion.

The patient's arm can be placed over the head with a restraint on the affected side. For an insertion line down the armpit (axillary line insertion), the patient's head is typically elevated from the bed by approx. 30° to 60°. Using an anesthetic needle and syringe, the physician may often initially insert a needle (aspirate) into the pleural cavity to check for the presence of air or fluid. Then, an incision can be made and in one embodiment a clamp can be used for opening the pleural cavity.

A chest tube can be positioned for insertion with the catheter guiding device according to the present invention and subsequently attached to a suitable suction-drain system. Chest tubes can in principle be inserted by using one of three different techniques: 1) Ultrasonic guided technique (including guide wire technique) 2) Trocar guided technique 3) Blunt dissection technique.

The ultrasonic guided technique is used for evacuation of pleural effusion, but is limited by the small diameter of the catheter and the procedure is associated with an increased risk of catheter clogging and this procedure normally represents a less effective evacuation.

The trocar technique is generally regarded as less safe and it is less popular due to an increased risk of e.g. iatrogenic lung injury, cf. herein above.

The blunt dissection technique is generally regarded as the most safe procedure for inserting a large diameter chest tube into the pleural cavity and this technique is preferred in most clinics and treatment centres.

The catheter guiding device used in the above-cited procedures is in one embodiment an S-shaped tube having a distal section, a mid section and a proximal section. The proximal section integrates a handle which points in the same direction, i.e. defines an proximal axial direction thereof, as the axial direction in which a catheter exits the extreme end of the distal section of the tube. In other words, the directions are the proximal axis and the distal axis are same.

The distal section of the guiding device is preferably a curved tube with an inner diameter a little wider than the outer diameter of a chest tube intended to be inserted into the lumen of the guiding device. In this embodiment, there is an entry port located in the mid section of the device for inserting a chest tube into the lumen of the guiding device.

The chest tube can be inserted into a body cavity through the exit port of the device when the device is inserted into the body cavity.

When the chest tube is advanced through the guiding device, the tip of the chest tube will, when exiting the device, point in the same direction as the direction defined by the proximal axis direction of the handle section (proximal section) of the device. This facilitates the chest tube to be inserted parallel to the lung surface and the chest wall, and not in the direction of the lung tissue or intrafissural area.

The inner surface of at least the distal section of the guiding device can be coated with a low friction coating material so as to facilitate a smooth insertion of the chest tube with a minimum of friction between the chest tube and the lumen wall of the guiding device. The outer surface of the distal section of the guiding device can also be coated with a low friction coating material so as to facilitate a smooth and less painful insertion of the guiding device between the ribs. Likewise, the catheter to be inserted can also be coated on the outer surface so as to minimise friction even further. Any state-of-the art friction reducing coating composition approved for medical applications can be used, including gels which attain a lubricating effect once they become wetted.

The method for chest tube insertion according to the present invention using the catheter guiding device according to the present invention is in one embodiment similar to the above-described, blunt dissection technique for the first steps (Steps 1 to 4 of the method cited on page 6 herein).

After the surgeon has explored the pleural cavity with a finger, the distal end of the catheter guiding device is inserted in the pleural cavity so that the exit port of the guiding device points in the direction intended for chest tube insertion and accurate location.

The chest tube can in one embodiment, as illustrated in FIG. 3, be inserted into the mid section of the guiding device in the direction towards the distal section. The chest tube is inserted through the catheter guiding device and the chest tube will enter the pleural cavity through the exit port located in the distal end of the device in a direction at least essentially parallel to the chest wall and the lung, pointing in the intended direction.

The direction of the insertion of a chest tube can in accordance with the present invention be monitored by observing i) the generally axial direction (proximal axis direction) of the handle, ii) the spatial position of the exit port of the device in the pleural cavity, iii) the angle of the handle relative to a horizontal position of the guiding device, iv) the side-ways movement of the handle relative to a position essentially perpendicular to the wall section of the pleural cavity, and v) the rotation of the guiding device.

The chest tube can be marked from the tip with distance indicators indicating the distance of a particular position of the chest tube from the tip of the chest tube. Distance indicators in centimeter or inch markings are routinely used. In this way, the medical practitioner will know how deep the chest tube is inserted into the chest cavity. When the chest tube is in place the catheter guiding device according to the present invention is immediately removed, while counter holding the chest tube in place. Finally the chest tube is sutured, followed by chest x-ray (as in the above-cited steps 8 and 9 as cited on page 6 herein).

Accordingly, the present invention provides a method comprising the following steps: 1) Disinfection and local anaesthesia in the skin in the 5th intercostal space anterior to the mid axillary line (the safe area). 2) Incision of the skin 3) Blunt dissection using a forceps through the thoracic wall to the pleural cavity. 4) A finger is inserted through the passage to verify that the pleural cavity has been entered. 5) The tip of the chest tube is entered into a guiding device according to the present invention and guided into the chest cavity in an intended direction. 6) The chest tube is accurately located in the chest cavity in an intended position. 7) The chest tube is sutured to the skin to prevent it from falling out. 8) Once the chest tube is in place a chest x-ray will be taken to check the location of the drain.

The guiding device can be produced in different sizes. A large chest tube (Ch 32) is in many cases preferred in case of trauma or large pneumothorax. A larger diameter chest tube is more effective at evacuating air and fluid, and the risk of clogging is reduced. However, smaller diameter chest tubes are sometimes preferred. Smaller diameter chest tubes are less painful and in many cases sufficient for effective evacuation.

In one embodiment the chest tubes according to the present invention are manufactured from a medical grade silicone material, such as a Platinum catalysed silicone material known to the person skilled in the art. Materials, such as PVC, EVA, polyurethane (PU), polyamide (PA), polyethylene (PE), and thermoplastic elastomers, such as e.g. TPU and TPE, can also be used. When used, these materials are normally, but not always, coated with silicone. An example is a silicone plated PVC. Materials according to the present invention can also use cross-linked silicones of a suitable hardness, cf. below. All of the afore-mentioned materials are available in approved, medical grade qualities.

Platinum catalysed Silicone represent one preferred embodiment of the present invention, but the Silicone can in principle also be catalysed by peroxide. However, this is less preferred as Silicone for used in medical applications must be free from peroxide bi-products and break-down products, such as chlorophenyls e.g. PCBs.

The below provided overview of preferred chest tube material functionalities provides a guidance for the skilled person only when selecting materials and the overview should not be narrowly construed when assessing the scope of protection conferred by the present invention.

In one embodiment it is preferred that the chest tube material for use in the present invention has a shore A hardness of from about 50 to about 80, such as from 50 to 60, for example from 60 to 70, such as from 70 to 80. Materials having suitable shore A hardness values outside these ranges can also be used.

In one embodiment it is preferred that the chest tube material for use in the present invention has a tensile strength at break of from about 7 to about 10 Mpa, such as from about 7 to about 8 Mpa, for example from about 8 to about 9 Mpa, such as from about 9 to about 10 Mpa. Materials having suitable tensile strength values outside these ranges can also be used.

In one embodiment it is preferred that the chest tube material for use in the present invention has an elongation at break of from about 600% to about 900%, such as from about 600% to about 700%, for example from about 700% to about 800%, such as from about 800% to about 900%. Materials having suitable elongation at break values outside these ranges can also be used.

In one embodiment it is preferred that the chest tube material for use in the present invention has a modulus at 200% elongation of from about 2 to 4 Mpa, such as from 2 to 3 Mpa, for example from 3 to 4 Mpa. Materials having suitable values of modula at 10 200% elongation outside these ranges can also be used.

In one embodiment it is preferred that the chest tube material for use in the present invention has a tear strength of from about 40 to 50 kN/M, such as from about 40 to 45 kN/M, for example from 45 to 50 kN/M. Materials having suitable tear strength values outside these ranges can also be used.

| Type of material CTM* | Silicone, Platinum Catalyzed ASTM* | Property | Unit | Value |
|---|---|---|---|---|
| 99 | D2240 | Durometer hardness, shore A | | 50-80 |
| 0137A | D412 | Tensile strength at break | MPa | 7-10 |
| 0137A | D412 | Elongation at break | % | 600-900 |
| 0137A | D412 | Modulus at 200% elongation | MPa | 2-4 |
| 0159A | D624 | Tear strength | kN/M | 40-50 |

*CTM: Corporate Test Method
*ASTM: American Society for Testing and Materials

Following insertion and correct and accurate positioning of a chest tube into the pleural cavity of an individual in accordance with the methods of the present invention, the guiding device can be removed and a silk suture can be used to hold the chest tube firmly in place.

The area is wrapped and an x ray may in some cases be taken to visualize the status of the chest tube placement and to confirm that complications have not occurred, such as e.g. pneumothorax, or to simply determine whether fluid has been successfully drained.

The correct positioning of a chest tube can also be confirmed using a computed tomography (CT) scan, but it is cumbersome and expensive to conduct such scans during or after the insertion of a chest tube into the pleural cavity of an individual. The present invention in one embodiment makes superfluous such CT scans as the present invention is capable of ensuring a higher success rate of chest tubes having been correctly and accurately inserted and located into the pleural cavity.

The free end of the chest tube is usually attached to an underwater seal, below the level of the chest. This allows air or fluids trapped in the pleural cavity to escape from the pleural cavity and the attachment of the chest tube to an underwater seal prevents said air and fluids from returning to the chest cavity. Alternatively, the tube can be attached to a flutter valve as is well known in the art. This allows patients with e.g. pneumothorax to remain more mobile.

A chest drainage device can be used to drain chest tube contents (air, blood, effusions). There are generally three chambers in such devices. The first chamber is a collecting chamber. The second is the "water seal" chamber which acts as a one way valve. Air bubbling through the water seal chamber is usual when the patient coughs or exhales but may indicate, if continual, a pleural or system leak that should be evaluated critically. It can also indicate a leak of air from the lung. The third chamber is the suction control chamber. The height of the water in this chamber determines the negative pressure of the system. Bubbling should be kept a gentle bubble to limit evaporating the fluid. Increased wall suction does not increase the negative pressure of the system.

Some improved chest drainage systems are designed so that they do not need the water seal chamber, i.e. there is no column of water that can spill and mix with blood, mandating the replacement of the canister. Preferred chest drainage devices are small and portable so the patient can be sent home for drainage if indicated.

Methods of Treatment and Methods for Performing a Diagnosis

The present invention is also directed to methods for treatment of an individual and methods for performing a diagnosis on an individual by examining ex vivo a fluid sample obtained from said individual.

Accordingly, the following invention also provides the below-cited methods for treating and/or diagnosing an individual suffering from a clinical indication in the pleural cavity which requires diagnosis and/or treatment.

In one aspect the present invention provides a method for treating or alleviating the symptoms of an individual, such as an animal or human being, suffering from a clinical condition associated with the pleural cavity, said method of treatment comprising the steps of inserting e.g. a pleural catheter or chest tube into the pleural cavity of the individual to be treated, and guiding the insertion of the pleural catheter by using the methods of the present invention for accurately directing a catheter to an intended position of a pleural cavity.

In another aspect the present invention provides a method for diagnosing a clinical indication, such as e.g. an infection and/or a malignancy, within the pleural cavity of an individual, said method comprising the steps of inserting a pleural catheter or chest tube into the pleural cavity of the individual, such as an animal or human being, by using the methods of the present invention for accurately directing a pleural catheter to an intended position within the pleural cavity, collecting a fluid sample from the pleural cavity of the individual by draining at least part of said pleural cavity with said pleural catheter or chest tube, analysing ex vivo said fluid sample, and diagnosing said clinical indication based on the result of said ex vivo analysis.

Patients suffering from a pleural effusion (accumulation of fluid in the pleural cavity), hemothorax (accumulation of blood in the pleural cavity), pneumothorax (collapsed lung), or empyema (accumulation of pus in the pleural cavity) can be treated in accordance with the methods of the present invention as these patient groups often require surgery in the form of insertion of a chest tube into the pleural cavity to provide relief from and/or to treat the observed symptoms.

In case of hydrothorax, hemothorax or chylothorax, the ideal location of the tip of the chest tube is close to the diaphragm, posteriorly in the pleural cavity, since this is the lowest point of the cavity. In case of pneumothorax, the ideal location of the tip of a chest tube is in the cranial, anterior part of the pleural cavity because air tends to be located at the top of the cavity. In case of empyema, the ideal location is into the empyema cavity which can vary in location from patient to patient.

Drainage of a pleural effusion is primarily done to relieve the symptoms of the effusion. The symptoms of a pleural effusion commonly include shortness of breath, chest pain, or dry cough. Drainage of a pleural effusion may also alleviate or terminate an inflammation cycle e.g. associated with a pneumonia-associated (parapneumonic) effusion. The fluid drained from a pleural effusion is in one embodiment of the present invention sent off for analysis and/or diagnosis and the fluid may thus provide valuable clues as to the likely cause of the effusion and the symptoms associated therewith.

Accordingly, drainage of a pleural effusion according to the present invention can be used in combination with a diagnostic test to evaluate a likely cause of the pleural effusion. Accordingly, in one embodiment, a cytopathological evaluation ex vivo of collected pleural fluid may be required in order to determine the causes of the abnormal accumulation of pleural fluid.

A cytopathological evaluation ex vivo can be carried out in combination with one or more diagnostic tests selected from e.g. clinical microscopy, microbiology, chemical analysis, tumor marker evaluation and pH determination. In one embodiment, the cause of e.g. an infection and/or a malignancy within the pleural cavity can be identified using the above-cited, diagnostic methods according to the present invention.

Relevant clinical conditions capable of being treated or diagnosed in accordance with the methods of the present invention are disclosed in more detail herein below.

Pneumothorax

A collection of air within the pleural cavity, arising either from the outside or from the lung, that causes the lung to collapse. Pneumothoraces may be traumatic, iatrogenic, or spontaneous. A tension pneumothorax is a particular type of pneumothorax where the air may enter (though a defect of the chest wall, lung, or airways) on inspiration, but cannot exit on expiration. Each breath increases the amount of trapped air in the chest cavity, leading to further lung compression. This is a medical emergency. Spontaneous pneumothorax is caused by a rupture of a cyst or a small sac (bleb) on the surface of the lung. Pneumothorax may also occur following an injury to the chest wall such as a fractured rib, any penetrating injury (gun shot or stabbing), surgical invasion of the chest, or may be deliberately induced in order to collapse the lung. A pneumothorax can also develop as a result of underlying lung diseases, including cystic fibrosis, chronic obstructive pulmonary disease (COPD), lung cancer, asthma, and infections of the lungs. Spontaneous pneumothorax affects about 9,000 persons each year in the U.S. who have no history of lung disease. This type of pneumothorax is most common in men between the ages of 20 and 40, particularly in tall, thin men. Smoking has been shown to increase the risk for spontaneous pneumothorax.

Tension Pneumothorax

A life-threatening condition that results from a progressive deterioration and worsening of a simple pneumothorax, associated with the formation of a one-way valve at the point of a rupture in the lung. Air becomes trapped in the pleural cavity between the chest wall and the lung, and builds up, putting pressure on the lung and keeping it from inflating fully Hydrothorax A condition that results from serous fluid accumulating in the pleural cavity. This specific condition can be related to cirrhosis with ascites in which ascitic fluid leaks into the pleural cavity.

Hemothorax

A condition that results from blood accumulating in the pleural cavity. Its cause is usually traumatic, from a blunt or penetrating injury to the thorax (chest), resulting in a rupture of the serous membrane either lining the thorax or covering the lungs. This rupture allows blood to spill into the pleural space, equalizing the pressures between it and the lungs. Blood loss may be massive in people with these conditions, as each side of the thorax can hold 30-40% of a person's blood volume. Even minor chest wall injury can lead to significant hemothorax. As most major hemothoraces are related to trauma, a rough estimate of their occurrence may be gleaned from trauma statistics. A rough estimate of the occurrence of hemothorax related to trauma in the United States approaches 300,000 cases per year.

Hemopneumothorax

The combination of two conditions: pneumothorax, or air in the chest cavity, and hemothorax, or blood in the chest cavity.

Pleural Empyema (Pyothorax)

An accumulation of pus in the pleural cavity. Most pleural empyemas arise from an infection within the lung, often associated with parapneumonic effusions. There are three stages: exudative, fibrinopurulent and organizing. In the exudative stage, the pus accumulates. This is followed by the fibrinopurulent stage in which there is loculation of the pleural fluid (the creation of grapelike pus pockets). In the final organizing stage, scarring of the pleural space may lead to lung entrapment.

Pleural Effusion

Fluid accumulation within the pleural space. Abnormal collections of pleural fluid may be due to excessive fluid volume (i.e. excess intravenous fluids, renal failure), decreased fluid protein (e.g. cirrhosis, proteinuria), heart failure, bleeding (hemothorax), infections (parapneumonic effusions, pleural empyema), inflammation, malignancies, or perforation of thoracic organs (i.e. chylothorax, esophageal rupture), inflammation, malignancies, or perforation of thoracic organs (i.e. chylothorax, esophageal rupture).

A Chylothorax (Chyle Leak)

A type of pleural effusion resulting from lymphatic fluid (chyle) accumulating in the pleural cavity.

Parapneumonic Effusion

A type of pleural effusion that arises as a result of pneumonia. There are three types of parapneumonic effusions: uncomplicated effusions, complicated effusions, and empyema. Uncomplicated effusions generally respond well to appropriate antibiotic treatment. Complicated parapneumonic effusions respond more variably: many resolve with antibiotics but may benefit from early pleural fluid drainage. Treatment of empyemas includes antibiotics, complete pleural fluid drainage, and reexpansion of the lung.

Pleuritis

An inflammation of the pleura. Pleuritis is frequently associated with the accumulation of extra fluid in the pleural cavity, also referred to as a pleural effusion.

Pneumonia

An abnormal inflammatory condition of the lung. It is often characterized as including inflammation of the parenchyma of the lung (that is, the alveoli) and abnormal alveolar filling with fluid (consolidation and exudation). Pneumonia can be caused by microorganisms, irritants and unknown causes. When pneumonias are grouped this way, infectious causes are the most common type. Occasionally, microorganisms infecting the lung will cause fluid (a pleural effusion) to build up in the pleural cavity. If the microorganisms themselves are present in the pleural cavity, the fluid collection is called an empyema. Pneumonia is a common illness which occurs in all age groups, and is a leading cause of death among the elderly and people who are chronically and terminally ill. Additionally, it is the leading cause of death in children under five years old worldwide.

Lung Cancer

A disease of uncontrolled cell growth in tissues of the lung. This growth may lead to metastasis, which is the invasion of adjacent tissue and infiltration beyond the lungs. The vast majority of primary lung cancers are carcinomas of the lung, derived from epithelial cells.

If the cancer grows in the airway, it may obstruct airflow, causing breathing difficulties. This can lead to accumulation of secretions behind the blockage, predisposing the patient to pneumonia. Lung cancer is the most common cause of cancer-related death in men and women.

Lymphangioleiomyomatosis (LAM)

A rare lung disease that results in a proliferation of disorderly smooth muscle growth throughout the bronchioles, alveolar septa, perivascular spaces, and lymphatics, resulting in the obstruction of small airways (leading to pulmonary cyst formation and pneumothorax) and lymphatics (leading to chylous pleural effusion). LAM occurs in a sporadic form, which only affects females, who are usually of childbearing age. LAM also occurs in patients who have tuberous sclerosis.

Tuberculosis

A common and often deadly infectious disease caused by mycobacteria, usually Mycobacterium tuberculosis in humans. Tuberculosis usually attacks the lungs but can also affect other parts of the body, causing other kinds of TB, collectively denoted extrapulmonary tuberculosis. This occurs more commonly in immunosuppressed persons and young children. Extrapulmonary infection sites include i.a. the pleura in tuberculosis pleurisy.

Additional lung conditions which may cause air or fluid to accumulate within the pleural cavity are listed herein below:

Acute bronchitis; Alpha-1 antitrypsin deficiency (an inherited disorder that can cause lung disease in adults and liver disease in adults and children); Asbestos Related Disorders; Chronic Bronchitis; Chronic obstructive pulmonary disease (COPD) (comprised primarily of three related conditions—chronic bronchitis, chronic asthma, and emphysema); Cystic fibrosis; Emphysema (subtype of chronic obstructive pulmonary disease); Killer Cold Virus: Adenovirus Infection (Ad14); Melioidosis or Whitmore's Disease (an infectious disease caused by a bacterium called Burkholderia pseudomallei); Pleurisy is inflammation of the pleura; Pulmonary fibrosis; Pulmonary edema; Pulmonary hypertension; Scleroderma; Severe acute respiratory syndrome (SARS); and Smoker's Lung.

Example

A device according to the present invention was tested and a catheter was inserted on a dead pig. The procedure disclosed below was adapted. An 80 kg pig that expired a few minutes before the testing, was positioned on the back. A passage to the pleural cavity through the right lateral chest wall was created by using the blunt dissection technique.

A total of 25 chest tube insertions (Ch32) were performed. The intended position of the tip of the chest tube was the top of the chest cavity, mimicking the ideal position in case of a pneumothorax. The distance from the skin incision point to the top of the pleural cavity was measured on the outer surface of the chest wall using the chest tube, and a pair of forceps was placed on the chest tube as a marker for the intended dept of the chest tube insertion.

The distal part of the device was inserted through the passage and the extreme end of the distal section was pointed in the direction of the top of the pleural cavity. The chest tube was inserted through the middle section, pointing in the direction of the distal section, and the chest tube was inserted until the intended depth.

After each chest tube insertion, an x-ray was performed (photo documentation) and the 10 chest tube was removed before the next insertion.

A total of 24 chest tube tips (96%) were positioned less than 2 cm from the extreme top, and 1 chest tube (4%) was positioned approximately 6 cm from the top.

In conclusion the vast majority of the chest tubes (96%) were accurately and precisely positioned. All 25 chest tubes were accurately positioned in an acceptable position.

The results shows, that the claimed method is excellent for inserting and accurately positioning chest tubes into the pleural cavity of an individual.

The invention claimed is:
1. A chest tube guiding device, comprising:
a proximal section including a proximal end;
a distal section including a distal end;
a lumen configured to receive a chest tube, wherein the lumen comprises at least one chest tube entry port and at least one chest tube exit port, and wherein the at least one chest tube exit port is separated from the at least one chest tube entry port by at least one section of the chest tube guiding device having a bent or curved section;

a mid-section located between the proximal end and the bent or curved section; and wherein the at least one chest tube entry port of the lumen comprises an opening in an outer wall of the chest tube guiding device, the opening in the outer wall being located at the mid-section of the chest tube guiding device, wherein the at least one chest tube exit port is located at the distal end, wherein the chest tube guiding device is configured to direct an insertion of the chest tube into the opening in the outer wall located at the mid-section and into a body cavity of a body of an individual when the chest tube exits the at least one chest tube exit port, wherein the bent or curved section has a projecting tip that is configured to facilitate an insertion of the distal end into the body cavity, the projecting tip comprising a lip located at the distal end, the lip extending distally from the at least one chest tube exit port, wherein a section of the outer wall includes at least one projecting collar or rim that is configured for insertion into the body of the individual and to facilitate positioning of the distal end into the body cavity, the at least one projecting collar or rim being located between the mid-section and the bent or curved section, and wherein the chest tube guiding device is configured to provide a positioning of the chest tube into the body cavity at a predetermined position.

2. The chest tube guiding device according to claim 1, wherein the body cavity is a pleural cavity of an animal or human body.

3. The chest tube guiding device according to claim 1, wherein the bent or curved section is substantially a circular arc or forms a distal angle measuring more than 0 degrees but less than 180 degrees.

4. The chest tube guiding device according to claim 1,
wherein a part of a distal section is tapered inwards along a direction of a distal axis from an edge close to the distal end until the distal end,
wherein the edge is a rounded edge, and
wherein the tapering is gradual over a distance of the distal section.

5. The chest tube guiding device according to claim 1, wherein the proximal section forms a proximal angle with the mid-section, and wherein the distal section forms a distal angle with the mid-section, the distal angle defining the bent or curved section.

6. The chest tube guiding device according to claim 5,
wherein the chest tube guiding device provides a functional relationship between a movement of the proximal end and the distal end,
wherein the functional relationship includes a measure of at least one of the proximal angle and the distal angle, and
wherein the measure of at least one of the proximal angle and the distal angle is more than 0 degrees but less than 180 degrees.

7. The chest tube guiding device according to claim 6, wherein the functional relationship is determined by a length of the distal section, and wherein the functional relationship:
determines a position of the distal end in the body; and
defines a direction in which the chest tube exits the at least one chest tube exit port, the direction being along a distal axis.

8. The chest tube guiding device according to claim 1, further comprising a removable bung in the lumen at the distal end of the chest tube guiding device.

9. The chest tube guiding device according to claim 1, wherein the inner surface of the chest tube guiding device surrounding the lumen comprises one or more projections, and wherein the one or more projections facilitate a movement of the chest tube within the chest tube guiding device.

10. The chest tube guiding device according to claim 1, wherein the chest tube guiding device is provided with indicia that are at least one of coloured and shaped to distinguish between the distal end and the proximal end.

11. The chest tube guiding device according to claim 1, wherein the proximal end, the lumen and the distal end are separable in two parts along an axial length of the chest tube guiding device.

12. The chest tube guiding device according to claim 1, further comprising a proximal bend located between the mid-section and the proximal end, wherein the proximal bend is bent in a different direction than the bent or curved section.

13. The chest tube guiding device according to claim 1, wherein the mid-section is an essentially straight connecting section.

14. The chest tube guiding device according to claim 1, wherein the proximal section includes a handle that is configured to be gripped during use of the chest tube guiding device.

* * * * *

UNITED STATES PATENT AND TRADEMARK OFFICE
CERTIFICATE OF CORRECTION

PATENT NO.         : 9,526,876 B2
APPLICATION NO.    : 13/697256
DATED              : December 27, 2016
INVENTOR(S)        : Peter Heydorn Kristensen et al.

It is certified that error appears in the above-identified patent and that said Letters Patent is hereby corrected as shown below:

On the Title Page

In item (73): Replace "Assignee: PIEURATECH APS, Arhus N (DK)" with
-- Assignee: PLEURATECH APS, Arhus N (DK) --

Signed and Sealed this
Fourteenth Day of March, 2017

Michelle K. Lee
*Director of the United States Patent and Trademark Office*